Figure 1:
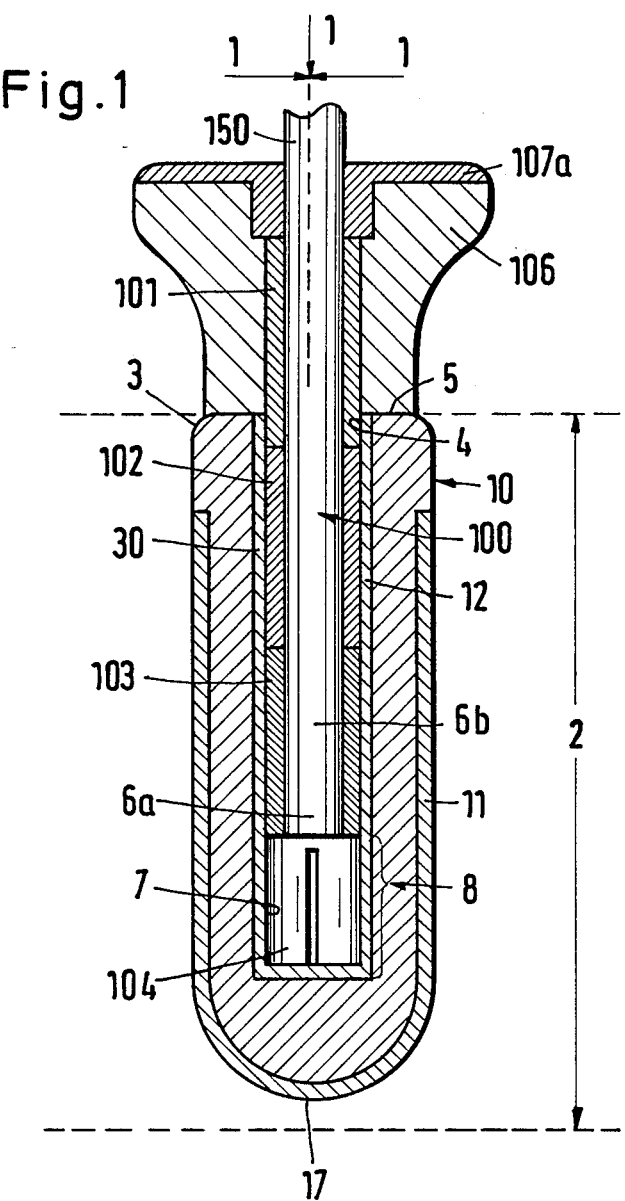

United States Patent [19]

Koch

[11] Patent Number: 4,731,085
[45] Date of Patent: Mar. 15, 1988

[54] ENOSSAL IMPLANT AND PROCESS FOR INSERTING AN ENOSSAL IMPLANT IN THE JAWBONE

[75] Inventor: Werner-Lutz Koch, Liebenau/Hanover, Fed. Rep. of Germany

[73] Assignee: Implanto-Lock Gesellschaft mit beschränkter Haftung für Implantatforschungund Entwicklung, Hamburg, Fed. Rep. of Germany

[21] Appl. No.: 795,650

[22] Filed: Nov. 6, 1985

[30] Foreign Application Priority Data

Nov. 9, 1984 [DE] Fed. Rep. of Germany ....... 3440952
Apr. 26, 1985 [DE] Fed. Rep. of Germany ....... 3515154
Sep. 10, 1985 [DE] Fed. Rep. of Germany ....... 3532125

[51] Int. Cl.⁴ .......................... A61F 2/28; A61C 8/00
[52] U.S. Cl. ..................................... 623/16; 433/173; 433/175; 433/177; 433/201.1
[58] Field of Search ............... 433/173, 174, 175, 176, 433/168, 169, 201.1; 623/16

[56] References Cited

U.S. PATENT DOCUMENTS 4,270,905  6/1981  Mohammed ..................... 433/173
4,543,379  9/1985  Gettleman et al. .......... 433/168.1 X Primary Examiner—Richard J. Apley
Assistant Examiner—Alan W. Cannon
Attorney, Agent, or Firm—Toren, McGeady & Associates

[57] ABSTRACT

The invention relates to an enossal implant, which comprises a primary cylinder (10) with a central longitudenal bore (13) which can be introduced into the jawbone and is anchored therein in positive and/or non-positive manner, as well as a secondary cylinder (100) insertable into the primary cylinder (10) and which has an oscillating rod (211) inserted and held in the longitudenal bore (13) and guide tube (30) of primary cylinder (10), said rod carrying an upper modular tube (220) made from an elastic material arranged at a distance from guide tube (30), accompanied by the formation of an air gap (225) and which is constructed at its free upper end for the connection of the dental prosthesis, whereas its lower end is connected in fixed or detachable manner to the primary cylinder (10), so that an implant is obtained which not only leads to a positive and non-positive connection to the bone and a load-free stabilization of the primary cylinder (10), but whose oscillating rod (211) absorbs the horizontal, vertical and torsional forces occuring in the mouth and diverts same into the bottom of the implant.

8 Claims, 32 Drawing Figures

U.S. Patent   Mar. 15, 1988   Sheet 1 of 13   4,731,085

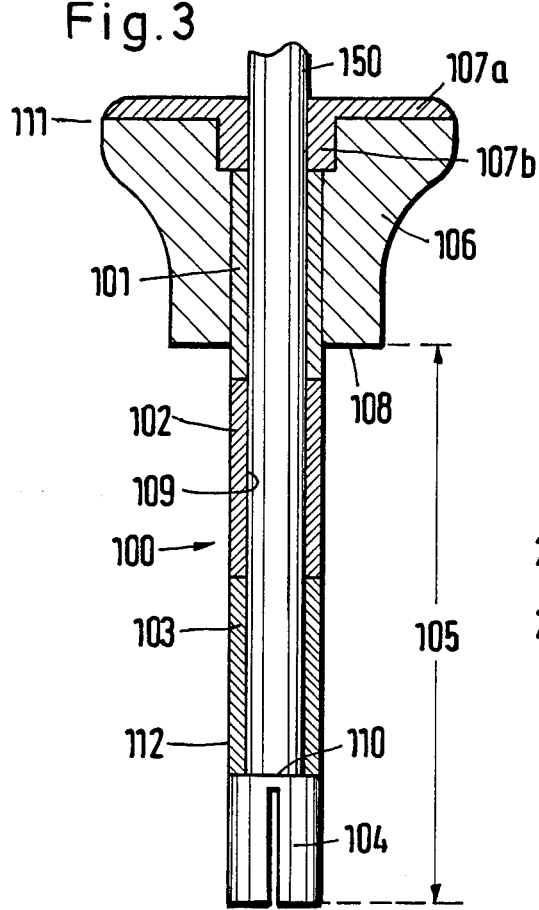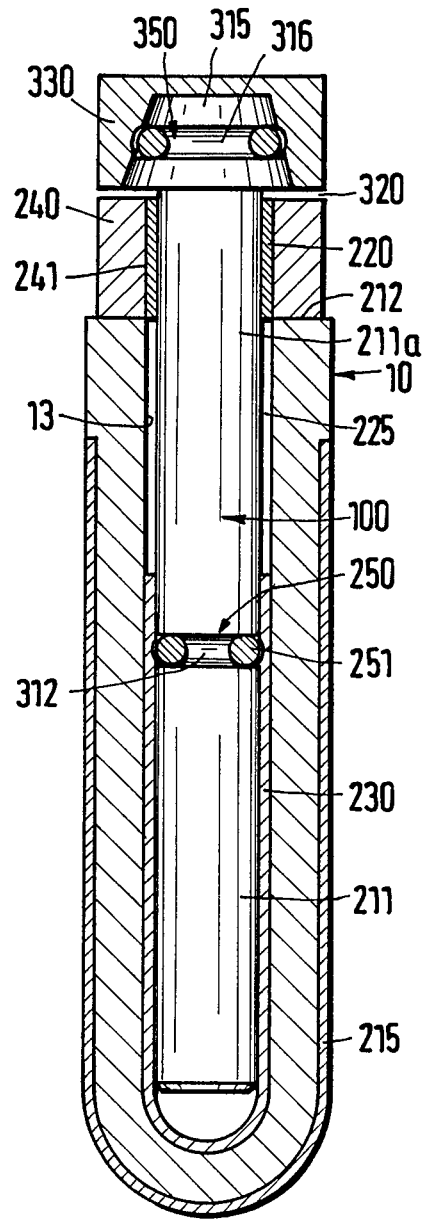

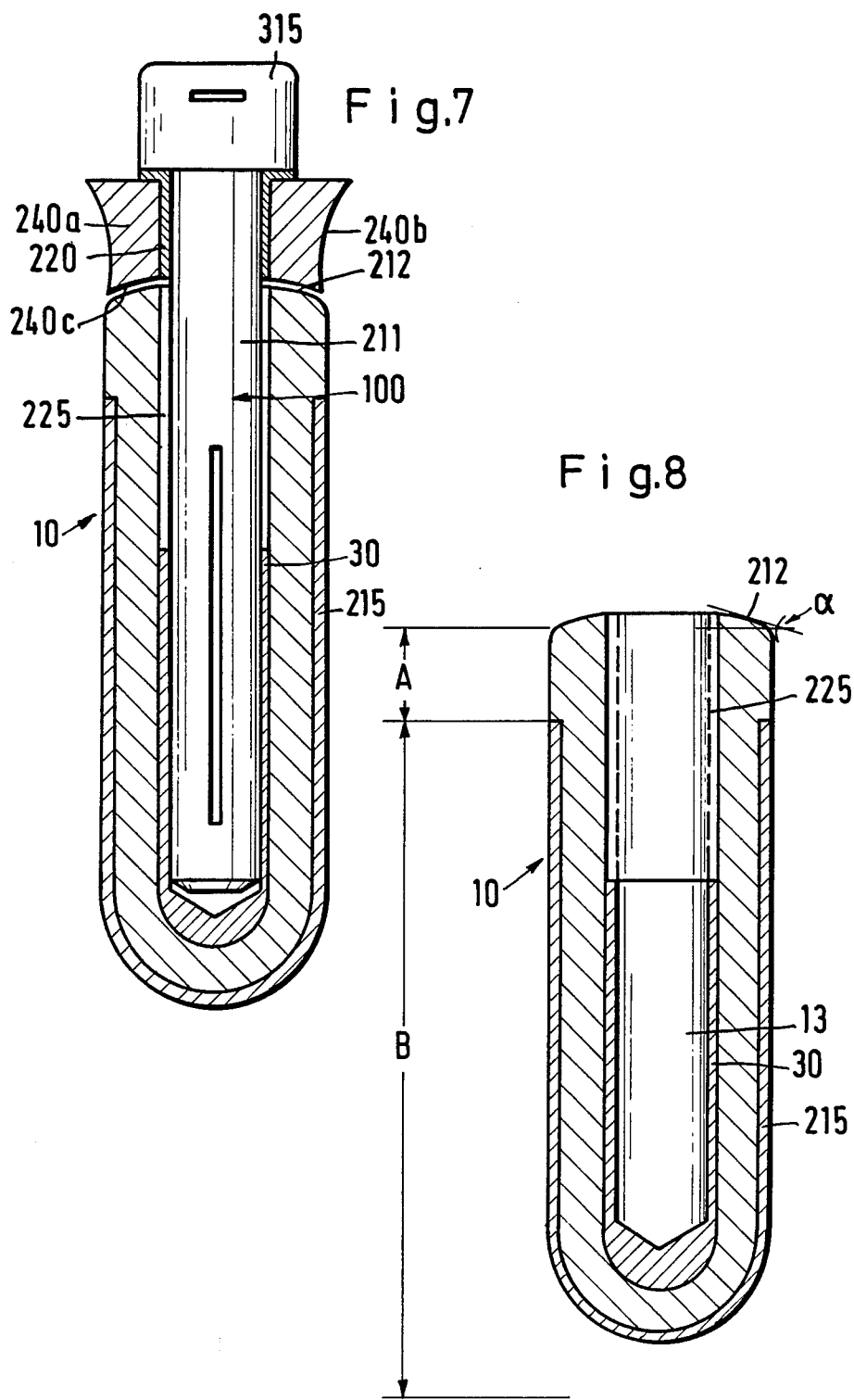

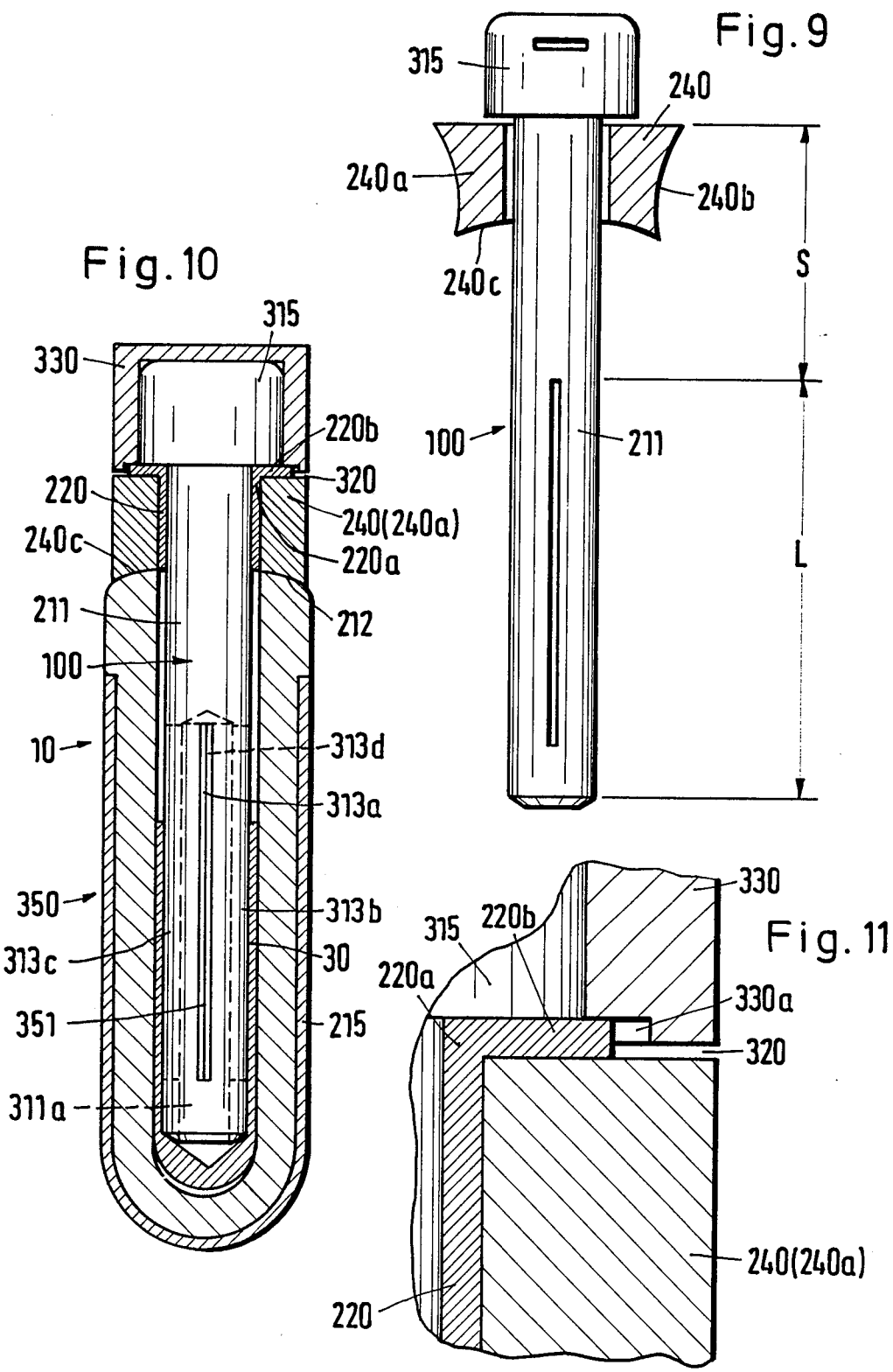

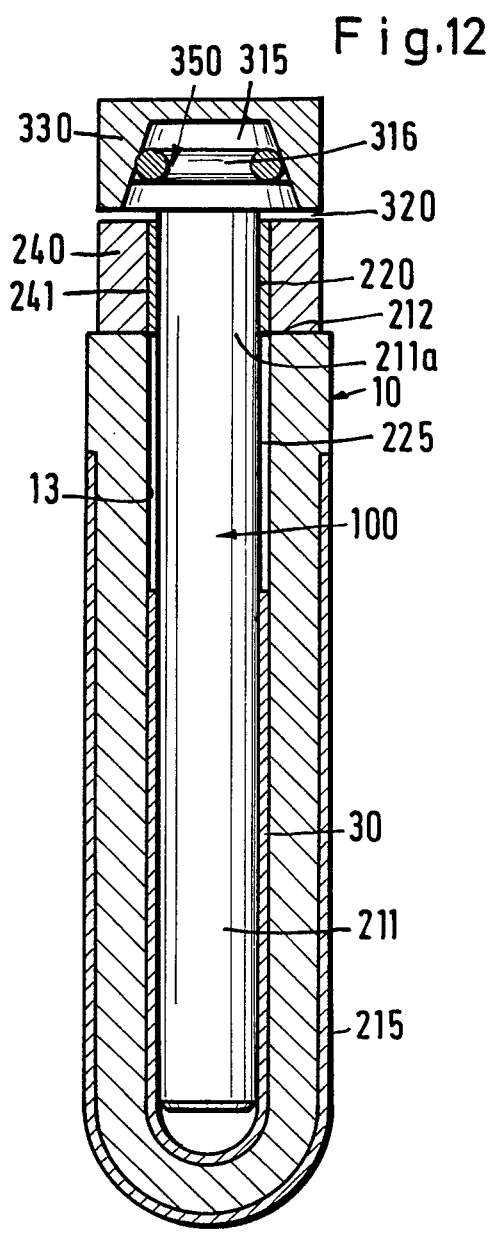
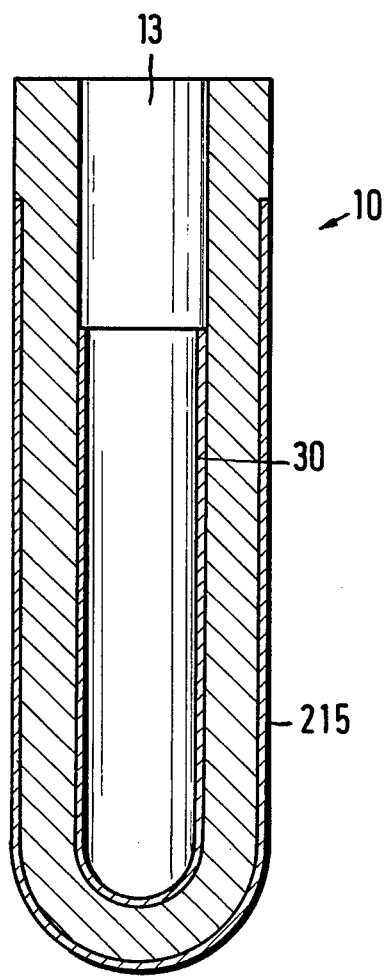

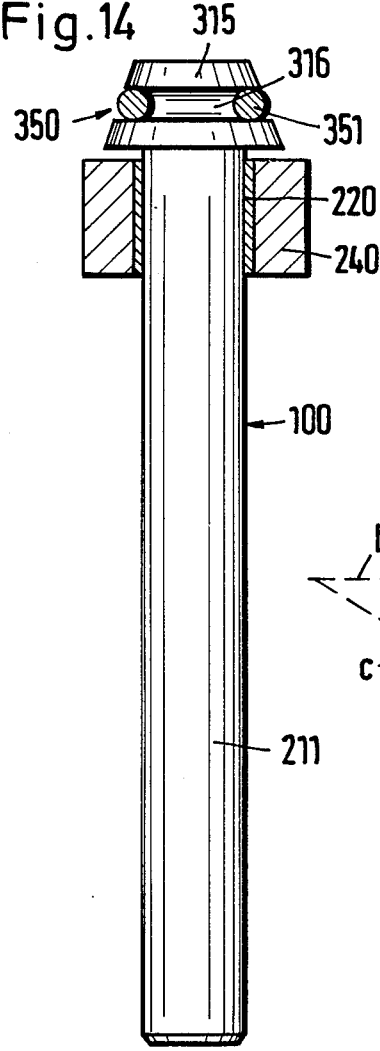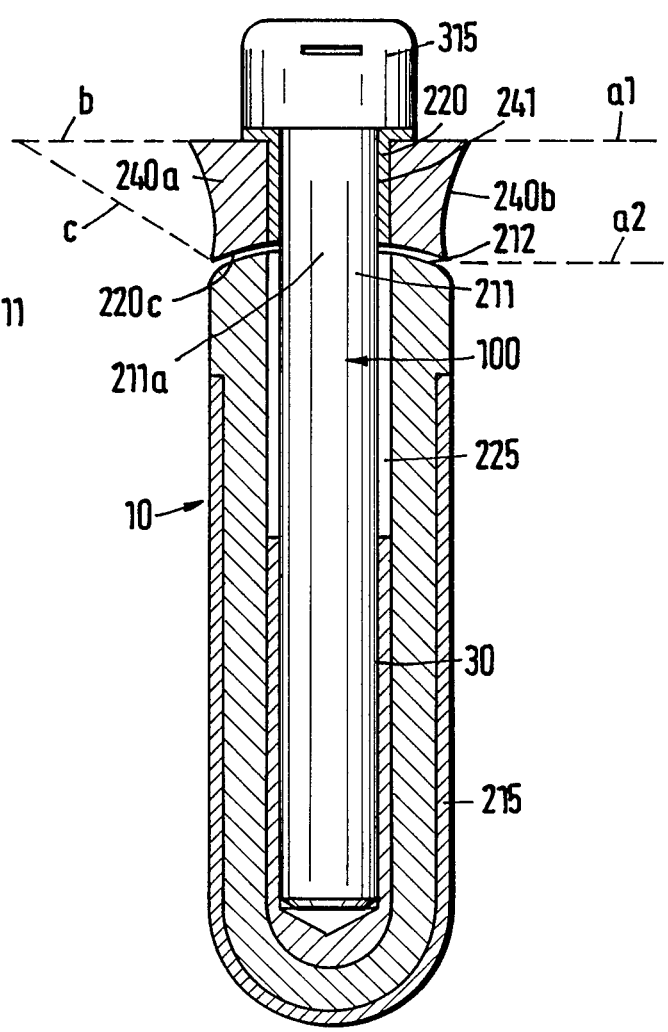

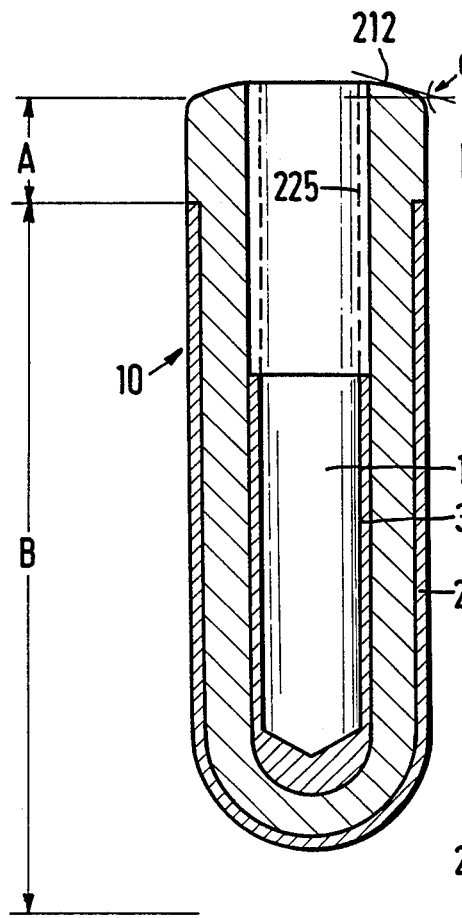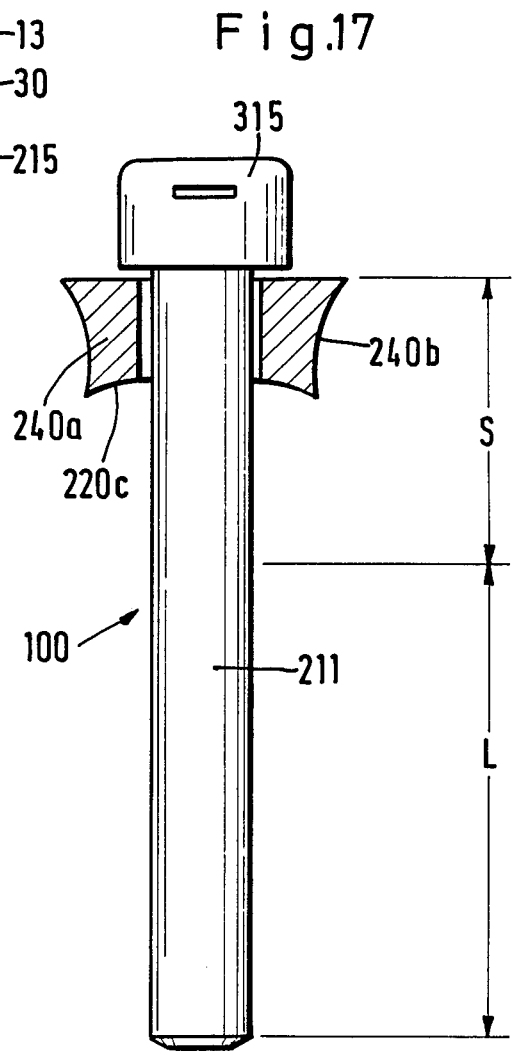

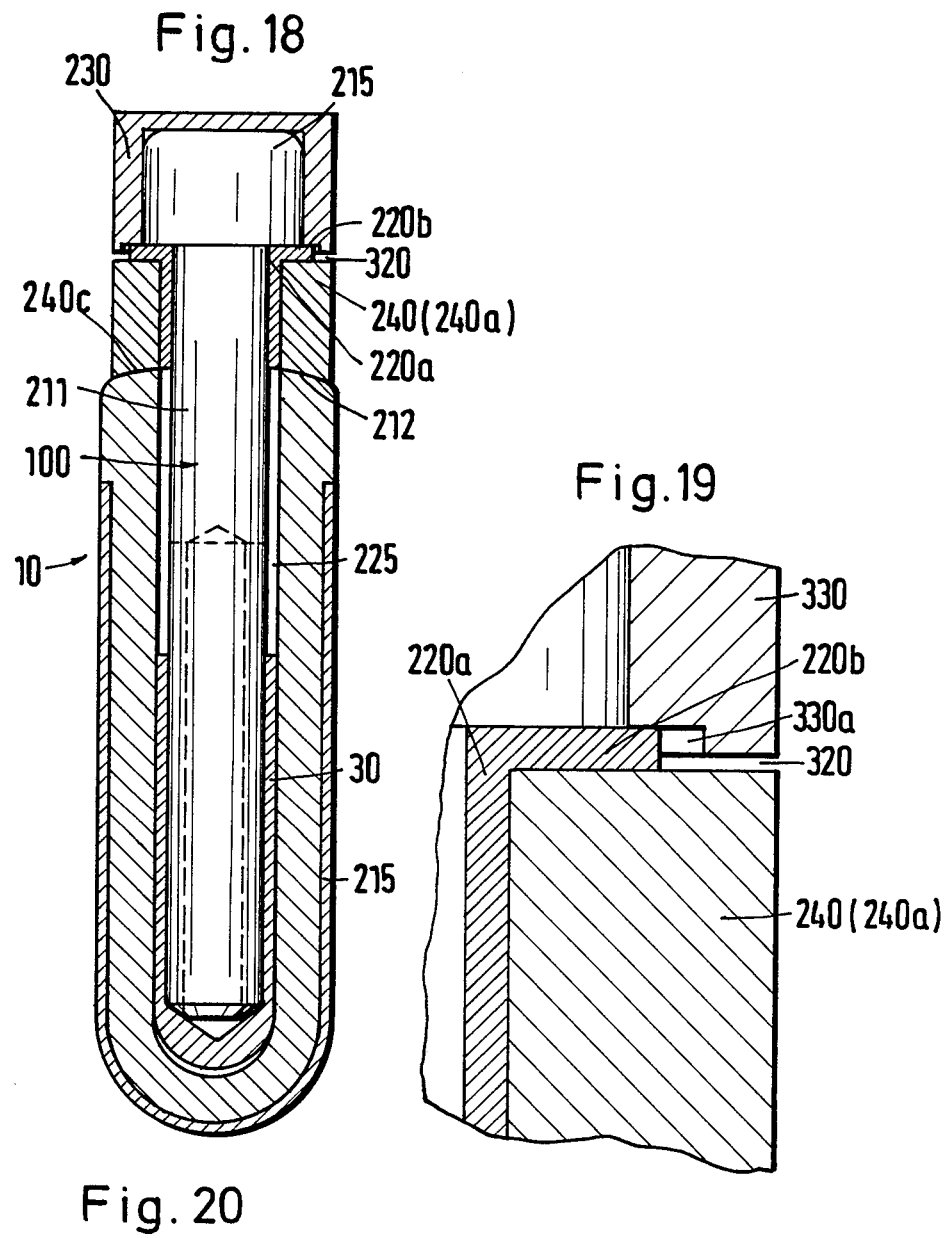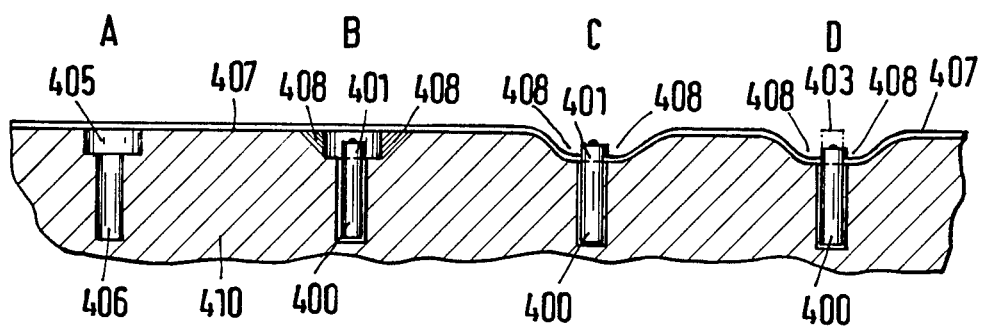

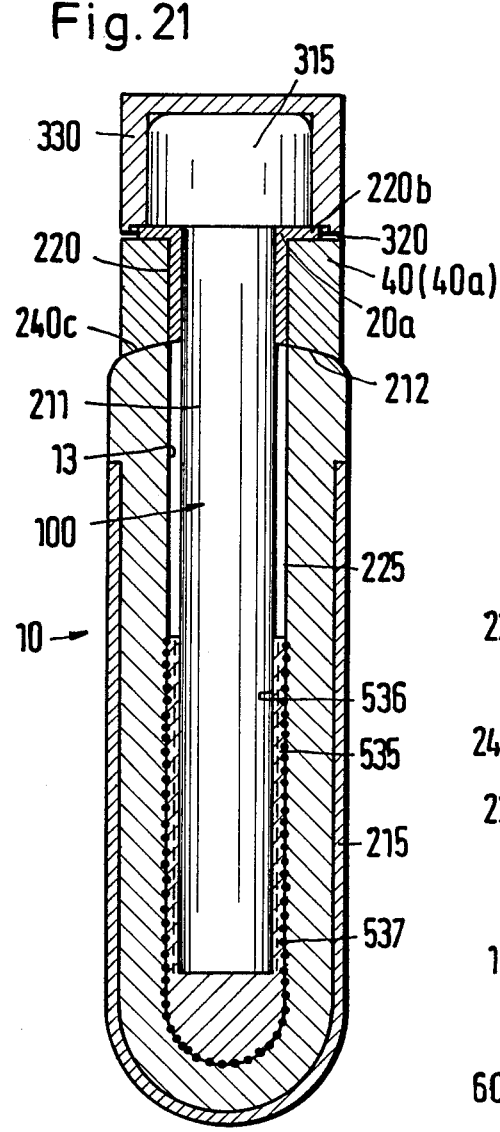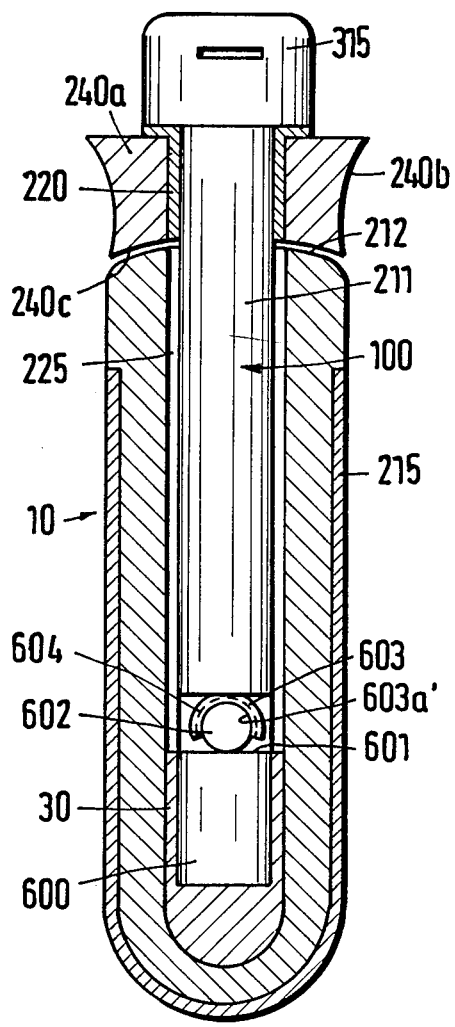

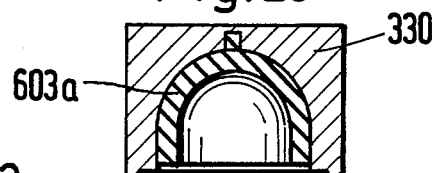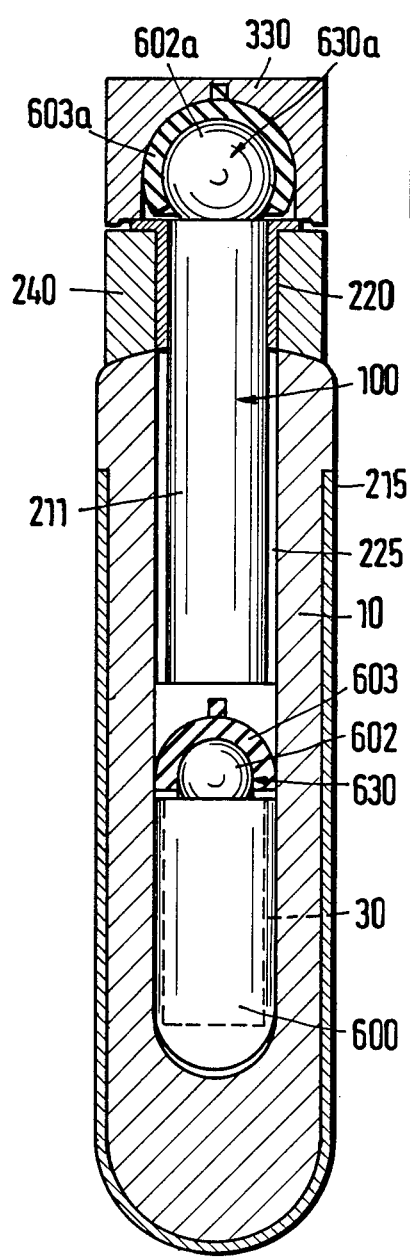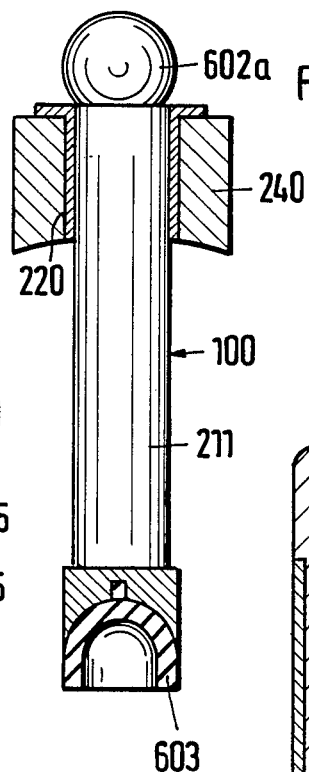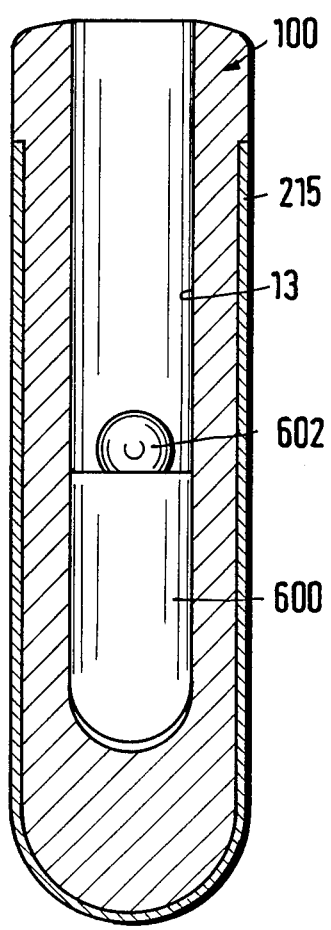

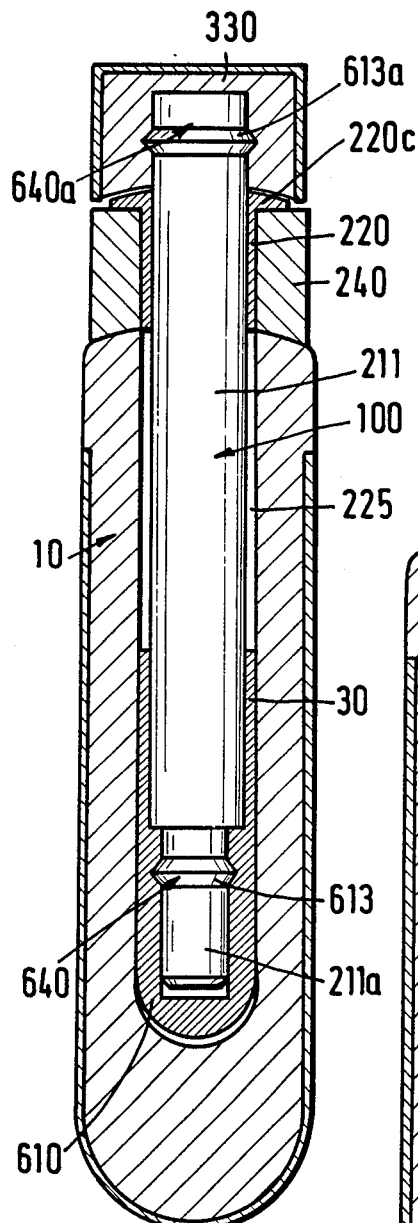
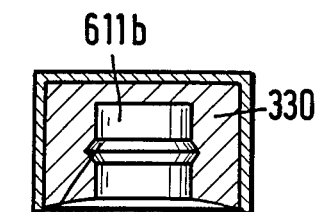
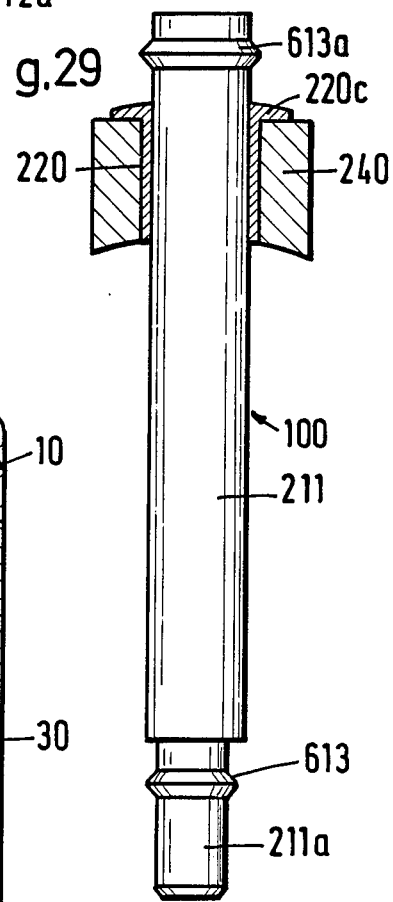
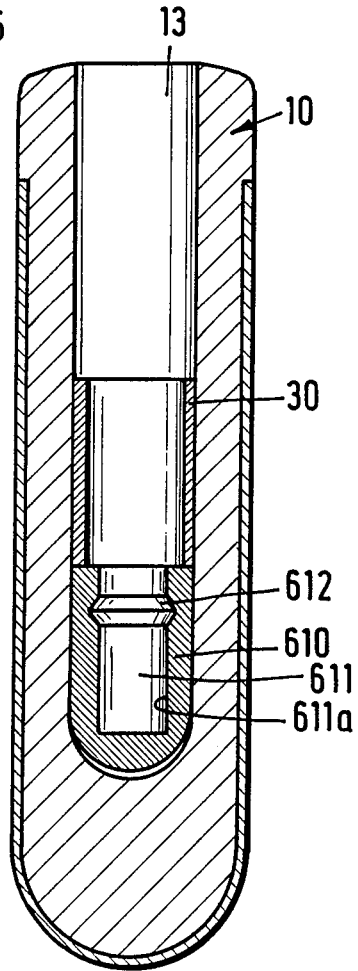

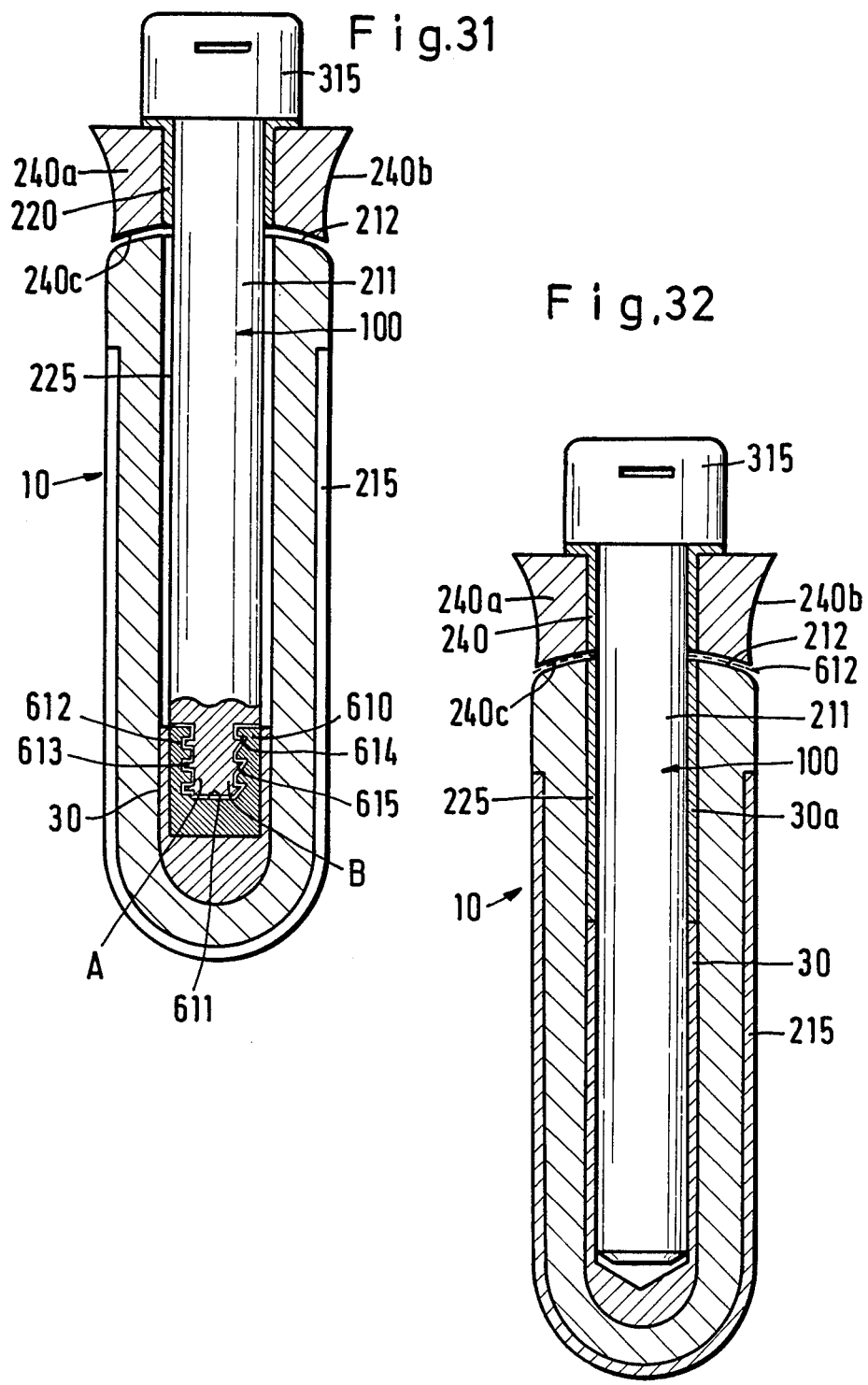

ENOSSAL IMPLANT AND PROCESS FOR INSERTING AN ENOSSAL IMPLANT IN THE JAWBONE

The invention relates to an enossal implant for securing a fixed or removable dental prosthesis, comprising two interconnectable parts, whereof one part is constructed in the form of a primary cylinder with a central longitudinal bore which is placed in the jawbone and anchored non-positively therein and the other part is constructed as a secondary cylinder, which can be placed in the longitudinal bore or the primary cylinder and has posts detachably held therein, being constructed at its free upper end for the connection of the dental prothesis, as well as to a process for inserting an enossal implant in the jawbone.

DE-OS No. 31 49 881 discloses a connecting element for enossal implants, with the aid of which a loosening of the implant through overloading the implant bearing and the resulting re-formation of the bone is to be prevented. Measures are provided for diverting forces acting on the dental prosthesis perpendicularly to the main axis of the implant into the interior of the latter, so as to bring about a uniform distribution of the stresses exerted by the implant on the implant bed. Therefore the dental prothesis is fixed to the spindle made from metallic materials, which passes co-axially through the inner area of a cup-shaped implant body and is pivotably mounted in a bed of elastic material filling the intermediate area between the spindle and the implant body, the pivot pin being formed from a rotary ball fixed to the spindle and whose diameter corresponds to the inside width of the implant body. However, it is a disadvantage of this implant that the lever fulcrum of the implant post is located roughly in the centre of the implant body, so that it is not possible to reliably prevent a loosening of the implant. It is also not possible to reliably ensure the removal of stresses which occur into the outer region of the implant body, so that damage can occur and in the case of a horizontal compression stress on the dental prothesis the implant body can break, particularly if the latter is made from a ceramic material.

The insertion of such enossal implants, which comprise a primary cylinder and a secondary cylinder, into the jawbone takes place in such a way that firstly a corresponding bore is prepared in the jawbone and then as the first phase the primary cylinder is inserted in the jawbone bore. This is followed as the second phase by the insertion of the secondary cylinder into the primary cylinder non-positively anchored in the jawbone. The prothesis mount is then screwed onto the connecting attachment of the secondary cylinder and then the prosthesis is joined therewith.

The problem of the invention is to provide an enossal implant comprising a primary cylinder and a secondary cylinder held therein, which leads to a positive and non-positive connection with the bone and in which a loadfree stabilization of the primary cylinder is ensured and the implant is non subject to plastic deformations and has a maintenance-free mechanism. A further aim is to ensure a fixed connection of the secondary cylinder pin in the primary cylinder longitudinal bore, without impairing the oscillating or vibrating property of the pin, the horizontal and/or vertical and/or torsional forces occuring in the mount being led off into the primary cylinder. In addition, a two-phase implantation process is to be provided using a predetermined and/or given anatomical behaviour of the jawbone (provoked atrophy), which ensures the physical activity in the same way as in the known two-phase implantation process.

To solve this problem, an enossal implant is proposed, which is constructed in such a way according to the invention that the implant post of the secondary cylinder is constructed as an oscillating rod or is surrounded by a force line system which diverts the horizontal and/or vertical and/or torsional forces and oscillations occuring in the vicinity of the dental prosthesis or in the mouth into the lower area of the secondary cylinder and from there into the primary cylinder or into the bottom thereof, said force line system comprising an elastic region or several strung together regions with different elastic properties, so that to a bottom, inelastic region are connected regions with inelasticity and the latter are then followed by regions with strong elasticity, the implant post or oscillating rod being fixed in the primary cylinder by means of a heat seal or is detachably held therein by means of an adhesive joint.

Further advantageous developments of the invention can be gathered from the subclaims, particular advantage being attached to the construction according to claim 2, in which the enossal implant is constructed in such a way that the implant post comprising a brittle material is surrounded by a tubular or annular force line system which diverts the oscillations occuring in the vicinity of the dental prosthesis due to the masseter muscle force acting thereon and whilst simultaneously displacing the lever fulcrum of the implant post into the lower region of the secondary cylinder and from there into the primary cylinder. This force line system has a plurality of strung together regions with different elastic characteristics, so that a bottom inelastic region is followed by regions with limited elasticity and the latter are then followed by regions with high elasticity. This construction leads to the following advantage. The force line system mounted on the implant post by means of a joining connection, e.g. a non-positive connection with anaerobic plastics, comprises a force line system, e.g. comprising a modular member or several modular members and in the latter case with different elastic properties. Of the superimposed modular members, the bottom modular member has no elasticity and has a rigid construction, like the implant post. The central modular member placed on the bottom modular member is made from a material with a limited elasticity, whilst the upper modular member is made from a very elastic material, so that under the action of masseter muscle forces, e.g. forces acting horizontally on the dental prosthesis, the fulcrum of the implant post acting as the lever is displaced into the lower region of the primary cylinder or implant body.

The rod-like implant post arranged in the secondary cylinder is made from a brittle material, such as e.g. surgical steel and forms a lever whose fulcrum is displaced into the lower third of the primary cylinder as a result of the specially constructed force line system. Due to the fact that the implant post is surrounded by modular members, e.g. modular tubes, modular rings, etc, which are made from materials with different elasticities, oscillations occuring on the implant post, e.g. in the case of chewing forces acting at right angles to the implant axis are intercepted, taken up by the force line system and diverted into the lower region of the primary cylinder. Thus, the modular members intercept the forces or divert them into the vicinity of the fulcrum, i.e. into the bottom of the implant or primary cylinder, without undergoing deformation or plastic deformation. Due to the modular members with different elastic properties which are used under force action there is a force reduction, the remaining forces being diverted via the implant post made from bending-resistant material to the fulcrum in the vicinity of the load or weight arm of the implant post.

Thus, an enossal implant comprising a primary cylinder and a secondary cylinder held therein and having a force line system is provided, in which there is a diverting of the force flux from the force introduction point in the vicinity of the dental prosthesis via the force line system within the secondary cylinder, then via the also force-diverting guide sleeve and via the primary cylinder into the bony implant bearing, so that apart from a reduction of the load peaks and apart from a reduction of overloading at the implant outlet point from the bone, the fulcrum of the implant post is displaced into the lower region of the implant.

The construction according to claim 7, in which the secondary cylinder pin is constructed as an oscillating rod is also very advantageous. On the pin is arranged an upper modular tube made from a highly elastic material and is joined to the pin by an adhesive joint. The primary cylinder is provided in the interior of its longitudinal bore and at a distance from the longitudinal bore inlet with a guide tube forming a modular tube-free portion forming an air gap with the secondary cylinder inserted. It is held in the primary cylinder by means of an adhesive joint. On the modular tube is arranged an implant attachment with a central through-bore aligned with the longitudinal bore of the primary cylinder and is slidingly held on the primary cylinder surface. The oscillating rod of the secondary cylinder is held in the guide tube by a heat seal arranged on the rod in the vicinity of the guide tube with the secondary cylinder inserted. As a result of an implant constructed in this way, a non-positive and/or positive connection of bone and implant is achieved, which is further improved by the external coating of the primary cylinder with a hydroxyl-apatite ceramic. In addition, the primary cylinder is stabilized in load-free manner and the secondary cylinder in a ready to assemble manner only comprises a single part. There is no need to join together several parts of the secondary cylinder in the mouth of the patient, so that easy, rapid manipulation by a fitter is ensured. There is also an optimum freedom from gaps as a result of the construction ensuring a constant tensile stress of the secondary cylinder against the primary cylinder as a result of the heat seal used, the sliding zones and by introducing the secondary cylinder into the primary cylinder under a clearly defined pressure. There is also an imitation of the paradontium through the sliding. There is an absolutely maintenance-free and non-wearing mechanism, because the implant only has elastically deformable parts, which are not subject to plastic deformation, so that there is no longer any need to replace plastically deformable parts. As a result of the maintenance-free mechanism of the implant, most of the after-care is obviated. This ensures a freedom from gaps and a considerable time saving for the fitter. The energy flows in the implant can be controlled, because plastically deformable parts are avoided, which helps the use of bioactively coated, body-friendly material alumina ceramic, which excludes any breakage risk. Due to the fact that the oscillating rod is anchored by the heat seal in the guide sleeve of the primary cylinder following the insertion of the secondary cylinder, vertical, horizontal and torsional forces of a dynamic nature acting on the oscillating rod oscillate the latter and are converted into heat, which is given off into the implant interior. Quantitatively small mechanical energies not converted into heat are supplied to the bone via the primary cylinder in the bearing zone and/or the sealing or securing point, the latter being best positioned in the vicinity of the vertical axis of the primary cylinder. The oscillation amplitudes are such that the primary cylinder is not mechanically stressed. The angular, all-round edge of the upper modular tube is used for compensating rod compression when vertical forces occur.

The paradontium is imitated by controlled sliding displacement of the implant attachment on the primary cylinder, damped by the permanent elastic upper modular tube. Through introducing the secondary cylinder into the primary cylinder under clearly defined pressure, freedom from gaps in the vicinity of the sliding zones is ensured by chemisorption. The air gap above the guide tube can be filled by a further modular tube made from a permanent elastic material, which then ensures the necessary sealing of the gaps.

The construction according to claim 16 is also advantageous, in which the pin of the secondary cylinder is constructed as an oscillating rod and on the pin is arranged an upper modular tube made from a highly elastic material and is connected thereto by an adhesive joint. The primary cylinder is provided in the inner region of its longitudinal bore with a guide tube, which is spaced from the longitudinal bore inlet, whilst providing a section forming an air gap free from a modular tube when the secondary cylinder is inserted. It is held in the primary cylinder by means of an adhesive joint. On the modular tube is placed an implant attachment with a central opening aligned with the longitudinal bore of the primary cylinder and which is slidingly held on the surface of the latter. The lower region of the secondary cylinder oscillating rod is fixed to the guide tube by an adhesive joint. As a result of an implant constructed in this way, a positive and/or non-positive connection between bone and implant is ensured, said connection being further improved by the external coating of the primary cylinder with a hydroxylapatite ceramic. In addition, the primary cylinder is stabilized in a laod-free manner and in a ready to assemble manner the secondary cylinder only comprises a single part. There is no need to join together several individual parts of the secondary cylinder in the mouth of the patient, so that easy rapid manipulation by the fitter is ensured. An optimum freedom from gaps is ensured by the construction, which ensures a constant tensile stress of the secondary cylinder against the primary cylinder through the heat seal used, the sliding zones and the introduction of the secondary cylinder into the primary cylinder under a clearly defined pressure. The paradontium is imitated by the sliding action. There is a completely maintenance-free and non-wearing mechanism, because the implant only has elastically deformable parts, which are not subject to any plastic deformation, so that there is no longer any need to replace pastically deformable parts. Due to the maintenance-free mechanism of the implant, most of the after-care is obviated. This ensures a freedom from gaps and also a considerable time saving for the fitter. The energy flows in the implant are controllable, because plastically deformable parts are avoided, so that the use of the bioactively coated, body-friendly material alumina ceramic is furthered, so that a breakage risk is excluded. Due to the fact that the oscillating rod is fixed to the primary cylinder guide sleeve after inserting the secondary cylinder, vertical, horizontal and torsional forces applied dynamically to the oscillating rod cause the latter to oscillate and the oscillations are converted into heat, which is given off to the interior of the implant. Quantitatively small mechanical energies not converted into heat are transferred via the primary cylinder to the bone in the bearing region or bonding point, which is best located in the centre of the vertical axis of the primary cylinder. The oscillation amplitudes are such that the primary cylinder is not mechanically stressed. In addition, the fixed connection of the oscillating rod to the guide sleeve fixed to the primary cylinder ensures that oscillations are better monitored, controlled and overcome.

The imitation of the paradontium takes place through the controlled sliding displacement of the implant attachment on the primary cylinder, damped by the permanent elastic upper modular tube. Through the introduction of the secondary cylinder into the primary cylinder under a clearly defined pressure, the freedom from gaps in the vicinity of the sliding zones is ensured.

It has been found that the ceramic upper parts, like a mucous membrane sleeve, can break under limited forces of e.g. 5 Kp, which is due to the fact that the spherical surface of the primary cylinder moves in wedge-like manner into the ceramic upper part in the case of a higher force expenditure, so that as a result of the wedge action which occurs the ceramic upper part can be broken.

However, it is not possible to eliminate the spherical surfaces, because the "rotary effect" of the implant ensures its universal usability. In addition to this there is the oscillation behaviour of the central oscillating rod, which freely oscillates and still freely oscillates in the implant in the case of horizontal forces which represent 250% of those conventionally encountered in the mouth, i.e. it can fully develop its damping action. It has been found that the sealing of the ceramic upper part against the ceramic lower part and the sliding characteristics (friction) cannot be modified by increased pressing of the upper part against the lower part and in fact only limited pressing is required to ensure the necessary sealing and sliding.

It was therefore necessary to intercept the vertical forces acting on the implant attachment or the oscillating head of the implant in the implant base and not on the ceramic upper part.

As a result of the construction given in claim 27, according to which the oscillating rod, even when the guide tube is omitted, is connected by means of a screw connection or some other suitable, equivalent connection to a shaped member with an upper bore for receiving the rod held in the interior of the primary cylinder by means of an adhesive joint and which fills the entire space used by the hitherto provided guide tube including the cavity below it between the bottom end of the otherwise provided guide tube and the primary cylinder bottom, the forces applied perpendicularly to the oscillating head of the implant are directly displaced to the implant bottom, the bottom of the primary cylinder being made from a ceramic material and said forces act at this point. Thus, pressure is relieved from the ceramic upper part. Only those forces resulting from the compression of the oscillating rod on force application to the oscillating or assembly head can have an effect.

However, there is only a slight reduction to the length of the oscillating rod, e.g. 41$\mu$ when a force of 80 Kp is applied. Such a compression is absorbed by the elasticity of the upper plastic modular tube, so that a pressure can no longer be exerted on the upper ceramic part, i.e. the mucous membrane sleeve, in such a way that it breaks. This construction also makes it possible to position the two ceramic parts of the implant in the form of spherical surfaces adjacent to one another, without the ceramic upper parts being unduly stressed and consequently breaking.

The process according to claim 33 for inserting an enossal implant in the jawbone for securing a fixed or removable dental prosthesis, in which the enossal implant comprises two interconnectable parts, whereof one part is constructed as a primary cylinder with a central longitudinal bore to be introduced into the jawbone and anchored therein in a non-positive manner, whilst the other part is constructed as a secondary cylinder having a pin which can be introduced into the longitudinal bore of the primary cylinder and is held therein and which at its free upper end is constructed for the connection of the dental prosthesis, comprises according to the invention that a depression is provided in the jawbone having a larger diameter than the implant to be inserted and has a depth which is less than the implant length. Centrally with respect to the milled depression, is milled the actual bore receiving the implant and has a diameter roughly corresponding to the external diameter of the implant. During a first phase the implant comprising a first cylinder and a secondary cylinder assembled outside the jawbone is inserted in the bore, so that the connecting attachment for the prosthesis comes to rest in the depression and the mucous membrane forms a top closure or seal. This is followed by a provoked bone atrophy with, during the course thereof, the release of the connecting attachment of the implant. In a second phase, the prosthesis mount is fixed and then the prosthesis is connected thereto.

The invention also relates to a process according to claim 34 for inserting an enossal implant in the jawbone for fixing a fixed or removable dental prosthesis, in which the enossal implant comprises two interconnectable parts, whereof one part is constructed as a primary cylinder with a central longitudinal bore to be introduced into the jawbone and anchored in non-positive manner therein and the other part is constructed as a secondary cylinder having a pin to be introduced into the longitudinal bore of the primary cylinder and held therein, whilst being constructed at its free upper end for the connection of the dental prosthesis. The secondary cylinder pin is constructed as an oscillating rod and on the pin is arranged an upper modular tube formed from a highly elastic material by adhesive connection to the pin. In the interior of its longitudinal bore, the primary cylinder has a guide tube at a distance from the longitudinal bore inlet and forms a section of which is module tube-free and forms an air gap when the secondary cylinder is inserted. It is held in the primary cylinder by means of an adhesive joint. Onto the modular tube is arranged an implant attachment with a central through-bore aligned with the longitudinal bore of the primary cylinder and is slidingly held on the surface of the latter. The lower region of the secondary cylinder oscillating rod is fixed to the guide tube by means of an adhesive joint. The construction is such that a depression is made in the jawbone which has a larger diameter than the implant to be inserted and said depression is milled with a depth which is less than the implant length. Centrally with respect to the milled depression is milled the actual bore receiving the implant with a diameter roughly corresponding to the external diameter of the implant. In a first phase, the implant comprising primary cylinder and secondary cylinder and assembled outside the jawbone is inserted in the bore, so that the connecting attachment for the prosthesis comes to rest in the depression and the mucous membrane forms a top closure. This is followed by a provoked bone atrophy and during the latter the joining attachment of the implant is released. In a second phase the prosthesis mount is screwed down and afterwards the prosthesis is connected thereto.

This process for inserting an enossal implant in the jawbone for securing fixed or removable dental prosthesis, in spite of the insertion in the prepared bore in the jawbone of the finished implant comprising primary cylinder and secondary cylinder constitutes a two-phase implantation process making use of a provoked bone atrophy. The two-phase implantation process is retained here, but the entirety of the actual implant is in fact implanted in the first phase. This is made possible by the predeterminable anatomical behaviour of the jawbone, where a provoked bone atrophy is involved, because whereas in the known implantation process initially the primary cylinder is implanted and then the secondary cylinder is inserted in the primary cylinder, in the process according to the invention the complete implant comprising primary cylinder and secondary cylinder is implanted in a first phase, so that healing of the implant in the jawbone can take place without stressing prior to the start of atrophy. As a result of the atrophy the head, i.e. the connecting attachment is released and simultaneously the mucous membrane is adapted to the atrophy which occurs and the resulting jawbone configuration. The second phase then comprises mounting the prosthesis mount on the implanted implant.

The invention is described in greater detail hereinafter relative to the drawings, wherein show:

FIG. 1 partly in elevation and partly in vertical section, an enossal implant comprising a primary cylinder and a secondary cylinder with a force line system comprising three modular tubes.

Figure 2:
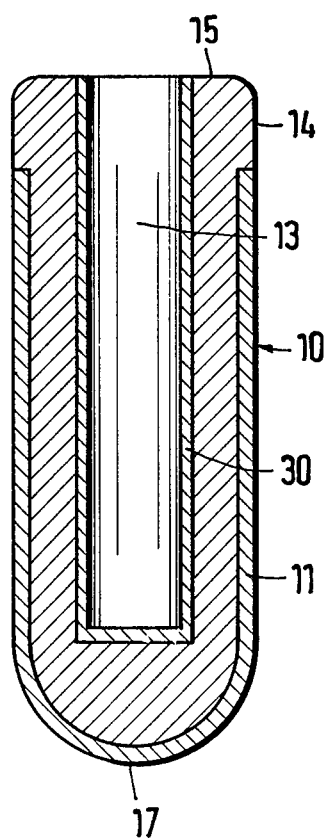

FIG. 2 in a vertical section the primary cylinder according to FIG. 1.

FIG. 3 in a vertical section the secondary cylinder according to FIG. 1.

FIG. 4 partly in elevation and partly in vertical section another embodiment of an enossal implant with a heat seal comprising a primary cylinder and a secondary cylinder with a pin constructed as an oscillating rod.

Figure 5:
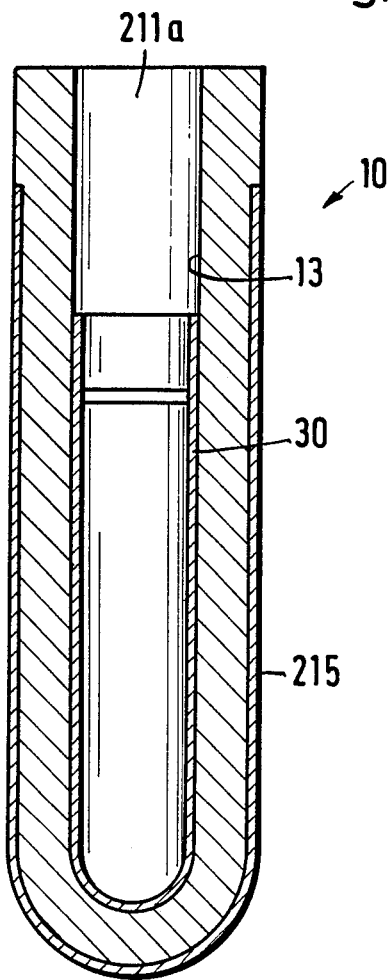

FIG. 5 in a vertical section the primary cylinder according to FIG. 4.

Figure 6:
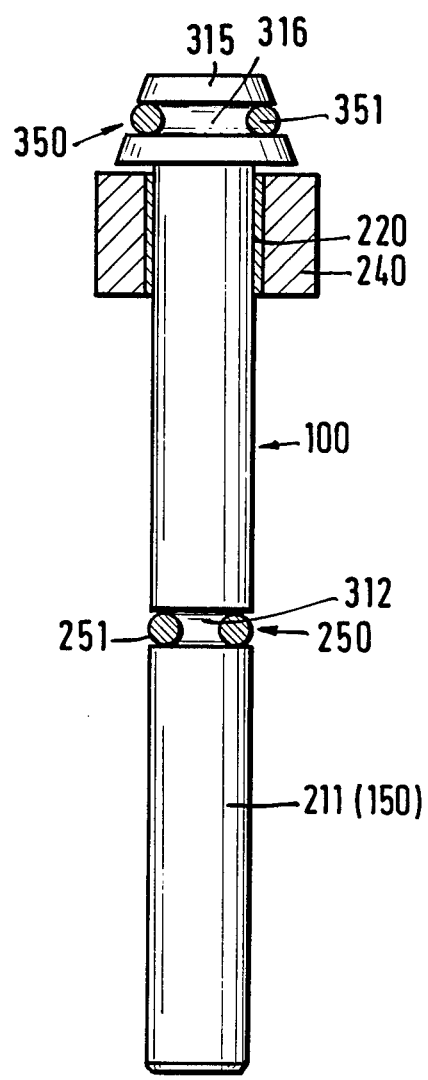

FIG. 6 in a vertical section the secondary cylinder according to FIG. 4.

FIG. 7 partly in elevation and partly in vertical section another embodiment of an enossal implant with spherical sliding surfaces.

FIG. 8 in a vertical section the primary cylinder of the implant according to FIG. 7.

FIG. 9 in a vertical section the secondary cylinder of the implant according to FIG. 7.

FIG. 10 partly in elevation and partly in vertical section, another embodiment of an enossal implant with a differently constructed heat seal.

FIG. 11 a detail of the transition region between the modular tube, implant attachment and secondary cylinder in the embodiment of FIG. 10.

FIG. 12 partly in elevation and partly in vertical section, another embodiment of an enossal implant comprising a primary cylinder and a secondary cylinder with an oscillating rod bonded into the guide tube.

FIG. 13 a vertical section of the primary cylinder according to FIG. 12.

FIG. 14 a vertical section of the secondary cylinder according to FIG. 12.

FIG. 15 partly in elevation and partly in vertical section, another embodiment of an enossal implant with an oscillating rod bonded into the guide tube and with spherical sliding surfaces.

FIG. 16 a vertical section of the primary cylinder of the implant of FIG. 15.

FIG. 17 a vertical section of the secondary cylinder of the implant of FIG. 15.

FIG. 18 partly in elevation and partly in vertical section, another embodiment of an enossal implant with bonded in oscillating rod.

FIG. 19 a detail of the transition region between the modular tube, implant attachment and secondary cylinder in the embodiment of FIG. 18.

FIG. 20 a diagramatic view of the individual process steps of the two-phase implantation process.

FIG. 21 partly in elevation and partly in vertical section, another embodiment of an enossal implant with an oscillating rod held in the primary cylinder by means of a base part.

FIG. 22 partly in elevation and partly in vertical section, an enossal implant in which the oscillating rod is held in the primary cylinder by means of a detachable clamp fastener.

FIG. 23 partly in elevation and partly in vertical section, another embodiment of an enossal implant in which the oscillating rod of the secondary cylinder is held in the primary cylinder and the assembly head on the oscillating rod by means of detachable clamp fasteners.

FIG. 24 partly in elevation and partly in vertical section, the secondary cylinder of the enossal implant of FIG. 23.

FIG. 25 partly in elevation and partly in vertical section, the primary cylinder of the enossal implant of FIG. 23.

FIG. 26 a vertical section of an assembly cap which can be placed on the oscillating rod of the secondary cylinder.

FIG. 27 partly in elevation and partly in a vertical section, another embodiment of an enossal implant, in which the oscillating rod of the secondary cylinder is held in the primary cylinder and the assembly head is held on the oscillating rod by means of undetachable clamp fasteners.

FIG. 28 partly in elevation and partly in vertical section, the primary cylinder of the enossal implant according to FIG. 27.

FIG. 29 partly in elevation and partly in vertical section, the secondary cylinder of the enossal implant according to FIG. 27.

FIG. 30 a vertical section of the assembly cap which can be placed on the secondary cylinder oscillating rod.

FIG. 31 partly in elevation and partly in vertical section, an enossal implant in which the oscillating rod is held in the primary cylinder by means of an undetachable spring catch.

FIG. 32 partly in elevation and partly in vertical section, an enossal implant with a device for bringing about a sealing of gaps in the vicinity of the spherical surfaces between the primary cylinder and the implant attachment.

The enossal implant shown in FIG. 1 comprises a primary cylinder 10, the so-called reception cylinder, and a secondary cylinder 100, the so-called working cylinder.

The enossal implant primary cylinder 10 comprises a bending-resistant body, which is normally made from alumina ceramic and which is externally coated with a hydroxyl-apatite ceramic, which is designated 11 in FIG. 2. This primary cylinder 10 is the actual implant body or material carrier and has a central longitudinal bore 13 forming the inner area (FIG. 2).

The secondary cylinder 100 is inserted in the longitudinal bore 13 of primary cylinder 10 following the implantation of the latter, i.e. approximately 3 months thereafter, so that the connection between the implant and the dental prosthesis is formed.

In the inner area or the longitudinal bore 13 of primary cylinder 10 is placed a guide tube 30, which roughly extends over the entire length of longitudinal bore 13 and inter alia permits the effortless insertion of the secondary cylinder 100 into the primary cylinder 10. This guide tube 30 also belongs to the force line system of the enossal implant which, like the hereinafter described modular members 101, 102, 103, 104 of the force line system can comprise different materials. As a result of the elastic deformation of the guide tube 30 comprising suitable materials in primary cylinder 10, it is possible to achieve an additional force reduction and the remaining forces are diverted into crystallographically specific directions, e.g. into the lower regions of the primary cylinder 10. When using and producing guide tube 30, considerable technical significance has been attached to so-called monocrystals of the material used, e.g. oscillatable or vibratable metal as an elastically deformable envelope for the secondary cylinder 100 mounted in the primary cylinder 10. It is in particular possible to grow and use monocrystalline materials with predetermined defects, so that the elastic deformation of guide tube 30 is controllable, e.g. in conjunction with the force transfer from secondary cylinder 100 to primary cylinder 10.

According to FIG. 3, secondary cylinder 100 has a pin 105, which can be introduced into bore 13 of primary cylinder 10, so that secondary cylinder 100 can be replaced. The diameter of the cylindrical outer wall 112 or part of the outer wall of pin 105 of secondary cylinder 100 is so much larger than the diameter of longitudinal bore 13 of primary cylinder 10, that pin 105 or part thereof, e.g. 104 is clampingly held at body temperature in the longitudinal bore 13, but in the case of a temperature reduction can be detached or removed from the primary cylinder longitudinal bore. Such a connection is of a relatively simple nature, it cannot be loosened and is substantially free from gaps, so that no bacteria forms and inflammation cannot occur.

The secondary cylinder 100 is formed by an implant post 150, whose upper free end carries a detachable sealing or locking device for the dental prosthesis which is not shown in the drawing. Moreover, the secondary cylinder 100 embraces an implant attachment 106, which comprises per se known materials, such as e.g. alumina ceramic. The top of the implant attachment 106 can be covered by a cover plate 107a, which is provided with an inwardly directed, neck-like extension 107b, which surrounds the upper area of the implant post 150 (FIG. 3).

Secondary cylinder 100 also houses the so-called force line system constituted by the modular members 101 to 104, which is particularly suitable for rotationally symmetrical cylindrical implants according to FIG. 1, which preferably comprise alumina ceramic, but can also be used for implants of other types or designs. This force line system with implant post 150 is a force-transferring, material binding element, which diverts the flux of force, namely from the force introduction point into the bony implant bearing 2, in such a way that the load peaks are reduced and there is no overloading of the outlet point 3 of the enossal implant from the bone (FIG. 1).

This force-transferring, material binding element of secondary cylinder 100 (FIG. 3) comprises modular members 101 to 104, which can be e.g. constructed in tubular or annular manner and are mounted on implant post 150. This force-transferring, material binding element can also comprise guide tube 30, in addition to the modular members 101 to 104. After introducing the secondary cylinder 100 into the longitudinal bore 13 of primary cylinder 10, the secondary cylinder 100 is surrounded and secured by guide tube 30, which is located in the longitudinal bore 13 of primary cylinder 10.

The force line system comprises superimposed modular members 101 to 104, which have roughly the same lengths, but have different elastic characteristics (FIGS. 1 and 3). The modular elements can also have different lengths.

The lower modular member 103 with or without part 104 is made from an inelastic material and is constructed in the same rigid manner as implant post 150. On said lower modular member 103 is placed a further, central modular member 102, which is made from a material with a limited elasticity. The third modular member, 101 is made from a very elastic material. The modular member can e.g. be made from a polycrystalline or monocrystalline material, a rigid plastic or some other suitable plastic with corresponding elastic characteristics. Adapted to the particular elasticity required, the other modular members are made from corresponding materials, it also being possible to use plastics, e.g. silicone rubbers, with differing degrees of hardness and elasticity. It is also possible to use other suitable materials and further reference will be made thereto hereinafter.

It is also possible to construct the modular members 101 to 104 in one piece and the then obviated force line system has three or more regions with different elastic characteristics. The lower region is then constructed inelastically, the central region has a limited elasticity and the upper region of the force line system has a high elasticity. The force line system extends with its upper modular member into implant attachment 106 (FIG. 3).

The guide tube 30 can also be guided into the region of implant attachment 106, i.e. the guide tube is also located in the implant attachment and during the assembly of secondary cylinder 100 is fixed to attachment 106. At the bottom, guide tube 30 is longer than the implant attachment 106, so that the guide tube projects by approximately 1 to 3 mm from the longitudinal bore 13 of primary cylinder 10 below the bearing surface of the implant attachment.

However, the guide tube 13 need not be led into the implant attachment 106. the guide supports are then constituted by the upper modular member 101, which engages in longitudinal bore 13 of primary cylinder 10 and is in metallic contact with guide tube 30 in primary cylinder 10, as indicated at 4 in FIG. 1. The guide tube brings the bearing surfaces of primary and secondary cylinders into absolute contact, particularly as these bearing surfaces 15, 108 of the primary cylinder 10 and secondary cylinder 100 are polished, so that there is a tight seal 5 between primary cylinder 10 and implant attachment 106 or secondary cylinder 100 (FIGS. 1 and 3).

The force line system obtained using modular members leads to the diversion of a masseter muscle force acting on implant post 150, indicated by arrows 1 in FIG. 1, e.g. a horizontally acting force. However, the implant post 150 of the enossal implant should be connected to neighbouring teeth or implants by a suitable dental prosthesis, so that by supporting on the neighbouring post, e.g. implant or tooth, it is possible to compensate the cause of a rotary movement or the so-called torque, a product of the force times lever or movement arm with respect to the rotation axis. During this post integration phase, the force acting e.g. the horizontal force is equally distributed over all the interconnected posts and the remaining proportion for the force line system or enossal implant acts in the region of the lower modular member 103, 104 comprising and inelastic material, e.g. a polycrystal and specifically in the lower third of the primary cylinder 10. This lower modular member 103, 104, like implant post 150, is made from a brittle material with a high modulus of elasticity. This leads to a uniformly distributed, greatly reduced stress in the bony implant mount or bearing 2 (FIG. 1).

The elastic deformation properties of modular members 101 to 104 when acting as so-called vibration dampers and the resulting uniform movement of the implant post 150 about its rest position, lead to a force diversion, which is linked with the reduction of the stress peaks, particularly if the lower modular member 103, 104 has a much higher modulus of elasticity than the overlying or upper modular member or is made from very brittle material, so that part of the action force is mainly diverted into the spherical base 17 of the enossal implant (FIGS. 1 and 2). A feature of the force line system is the implant post 150, which is surrounded by the different modular members 101 to 104, which does not undergo a shape and configuration change under force action and which acts in a mainly oscillating manner after assembly of the complete system, whilst the modular members undergo elastic deformation.

The implant post 150 can comprise a polycrystalline material, e.g. a metal with a high modulus of elasticity. It has been shown that the plastic characteristics of the metallic material used with a monocrystalline or polycrystalline structure is determined by factors, which lead to the differences between the real lattice and the ideal lattice. These more particularly relate to the different types of lattice defects, which partly result from the crystal growth, but partly are formed by external effects, e.g. the manufacture and processing of the metal. Each lattice defect is a component for the plastic behaviour of a material under the action of forces, which are well below the theoretical shear strength of a so-called monocrystal. Most metals or crystals have plasticity. If external forces act on metallic bodies, e.g. on implant post 150, then there is a permanent change to their shape before the start of break, unlike in the case of brittle materials e.g. implant post 150 where break occurs on exceediing specific stress limit.

Thus, if in the case of a plastically deformed body, the force acting thereon is removed, the deformations only partly return to the original shape and mostly they are left as so-called shape changers, whereas the deformations are removed again on removing the force in the case of elastically deformed members, e.g. implant post 150. Thus, implant post 150 is made from a brittle material. The thickness of the implant post 150 is based on a specific stress limit, the masseter muscle force being assumed as the external force. As a result of the cross-section and length of implant post 150, the exceeding of a specific stress limit and consequently the breaking of the implant post is prevented and under these conditions, the post oscillates as a body with uniform movement about its rest position.

If a polycrystalline body, e.g. the implant post 150 is plastically extended by a tensile strain, it is uniformly constricted on all sides. However, a monocrystal, e.g. a tubular modular member 101 to 103 or an annular modular member, assumes an elliptical cross-section. In the case of a monocrystal e.g. the thin, oscillating metal sheet of modular members 101 to 104 and guide tube 30, crystallographically defined planes of the lattice, the so-called sliding planes, slide on one another in crystallographically defined directions, i.e. the sliding directions. This process is e.g. of significance in the case of a masseter muscle force 1 on implant post 150 and modular members 101 to 104, as well as guide tube 30 in primary cylinder 10. It has been found that the monocrystals have a major technical significance as an elastically deformable envelope of implant post 150, i.e. the complete force line system formed from modular members 101 to 104. The force line system is in part the elastically deformable intermediate layer between implant post 150 and primary cylinder 10. Through the use of suitable metallic materials, e.g. monocrystals with predetermined defects and so-called impurities, the elastic deformations of the modular members and guide tube 30 can be controlled in conjunction with the characteristic mobility of the teeth or the intramobility of further implants. Whether and to what extent a crystal or material from which is formed the modular members and guide tube or tubes is deformable, is dependent on factors such as e.g. the structure, temperature, deformation type, etc.; it being possible to use a multipart guide tube instead of a one-part tube.

If in the force line system a modular member is exposed to a force, e.g. the oscillation of implant post 150, then the modular member undergoes shape changes, i.e. the thin, oscillatable metal from which the modular member is made is elastically deformed. If during the deformation the forces acting on the modular members do not exceed the quantity or a specific quantity, then this constitutes an elastic or reversable deformation. However, if the elastic limit is exceeded, there is either a plastic deformation or the material/the modular member or guide tube/primary cylinder of the enossal implant is broken. Thus, the elastic shape changes or deformations of modular members 101 to 104 are dependant on the structure of the material Apart from monocrystalline materials, it is also possible to use polycrystalline materials for producing the modular members.

The fixing of secondary cylinder 100 in the inner area or in the longitudinal bore 13 of primary cylinder 10 takes place by means of a per se known device, which can e.g. be constructed as a heat seal or thermal closure and as shown at 104 in FIG. 3. For fixing secondary cylinder 100, it is possible to use jointing connections 110, such as e.g. an integral joint with anaerobic plastics or other suitable materials.

Implant post 150 and the lower modular member 104 are made from a brittle material with a high modulus of elasticity and both are made from materials with the same modulus. If a force 1 acts in the upper region of the dental prosthesis, the implant post 150 acts as a lever. The lever fulcrum is located approximately in the lower third of primary cylinder 10, if e.g. the lower modular member and implant post 150 are made from brittle material with a high modulus of elasticity and the modular members 101, 102, 103 above same are made from elastically deformable materials. The lever fulcrum located in the lower third of primary cylinder 10 is indicated at 6a in FIG. 1.

Due to the fact that implant post 150 is fixed to the lower modular members 104 and 110 (FIG. 3), e.g. by means of jointing connections or the like and in turn both are clamped into guide tube 30 in primary cylinder 10, as indicated at 7 in FIG. 1, a further auxiliary fulcrum 6b is formed in the case of a horizontal force action in the upper region of the dental prosthesis. If the implant post 150 is disturbed by the force action at the dental prosthesis, the implant post 150 transfers the oscillations to the lower modular member, which starts to oscillate as a result of its fixed fitting in guide tube 30 of primary cylinder 10 and the same modulus of elasticity as implant post 150. A plurality of oscillation fields form, namely one around the actual lever fulcrum 6a, one around the auxilary fulcrum 6b and another in the overall area of the lower modular member. As a result the force is vertically displaced downwards and over the lower modular member 104, passing over the entire length of the lower modular member to primary cylinder 10 and from there to the bones.

The centre of the lower modular member 103 is located in the so-called rotation centre 6b of the implant, which is in turn located in the centre of primary cylinder 10. By means of implant post 150 and the lower modular members 103, 104, there is a vertical force displacement and simultaneously a force distribution, so that a force occuring at the force application point 1 or on the dental prosthesis only acts with part of the original force in the force dispensing region (FIG. 1).

The enossal implant shown in FIGS. 4 to 6 also comprises a primary cylinder 10 and a secondary cylinder 100.

Primary cylinder 10 comprises a bending-resistant body, particularly an alumina ceramic and is externally coated with hydroxyl-apatite ceramic. This external coating is designated 215. As can be gathered from FIG. 5, the external coating 215 does not extend over the entire area of the primary cylinder 10 and further reference will be made to this hereinafter.

Primary cylinder 10 is located in the actual implant body and has a central longitudinal bore 13, which forms the inner area.

Following the implantation of the primary cylinder 10, i.e. approximately 3 months thereafter, secondary cylinder 100 is inserted in longitudinal bore 13 of primary cylinder 10, so that the connection between implant and dental prosthesis is formed.

The secondary cylinder 100 has a pin constructed as an oscillating rod 211 or an implant post 150, on which is arranged an upper modular tube 220, which is made from a highly elastic material, which can also be of a metallic, plastic or other nature. This modular tube 220 is positioned in the upper region of the oscillating rod 211 of secondary cylinder 100 and is held thereon by means of an adhesive connection.

In the inner area of longitudinal bore 13 of primary cylinder 10 and in fact spaced from opening 211a of bore 13 is provided a guide tube 30. The section between modular tube 220 and guide tube 30 is free from any modular tube and forms an air gap 225 (FIG. 4) when secondary cylinder 100 is inserted in primary cylinder 10. Guide tube 30, which extends over a larger part of the length of primary cylinder 10, is fixed in the latter by means of an adhesive joint.

The secondary cylinder 100 comprises a pin insertable in the longitudinal bore 13 of primary cylinder 10 and which is constituted by an oscillating rod 211 made from suitable materials and forms an upper head-like extension 315 or oscillating head, which forms the fitting head, and which receives a fitting cap 330, which is detachably held on the oscillating head 315.

The implant attachment 240 is mounted on modular tube 220 and is provided with a central through-bore 241 corresponding to the external diameter of tube 220. In the embodiment of FIGS. 4 and 6, implant attachment 240 has a cylindrical shape and an external diameter roughly corresponding to the external diameter of primary cylinder 10. However, the external diameter of implant attachment 240 can also be smaller than that of the primary cylinder 10, so that then the external diameter of implant attachment 240 coincides with that of the fitting cap 330. The latter is made from metallic materials, particularly precious metals.

Whereas in the implant embodiment of FIGS. 4 and 5 the sliding surface 212 in the upper region of primary cylinder 10 is at right angles to the longitudinal axis of cylinder 10 and therefore runs horizontally, the sliding surface 212 of primary cylinder 10 for implant attachment 240a according to the embodiment of FIGS. 7 and 8 and is constructed as a cup with an angle $\alpha$ of in particular 9.27°. In this embodiment, the upper implant attachment 240a (FIG. 9) is constructed as an approximately cylindrical shaped member, whose external wall surface 240b is drawn in arcuately and whose lower external diameter corresponds roughly to the external diameter of primary cylinder 10, whereas the upper external diameter of implant attachment 240a is larger than the lower external diameter. In addition, the lower bearing surface 240c of implant attachment 240a is adapted to the sliding surface 212 of primary cylinder 10, so that a completely satisfactory sliding of attachment 240a on cylinder 10 is ensured. Thus, implant attachment 240a is sliding held on the surface of primary cylinder 10.

Oscillating rod 211 of secondary cylinder 100 is anchored in guide tube 30. The external diameter of oscillating rod 211 is smaller than the internal diameter of longitudinal bore 13 of primary cylinder 10, so that the oscillating rod 211 is held in a firmly seated manner in longitudinal bore 13 of cylinder 10.

In addition, the oscillating rod 211 of secondary cylinder 100 is held in primary cylinder 10 by means of a heat seal 250 (FIGS. 4 and 6). Heal seal 250 is located roughly in the centre of the primary cylinder 10 or guide tube 30 and comprises a bimetallic wire 251 (e.g. memory metal), which is held in an annular slot 312, which is formed in the oscillating rod 211. In the same way as oscillating rod 211 is held by heat seal 250 in primary cylinder 10, the fitting cap 330 is held on the fitting head 315. Heat seal 350 also comprises a bimetallic wire 351 (e.g. of memory metal), said wire 351 being held in an annular slot 316 in fitting head 315 (FIG. 6). As shown in FIG. 6, fitting head 316 tapers conically upwards.

The outer coating 215 on primary cylinder 10 is in particular of hydroxyl-apatite ceramic. As shown in FIG. 8, this outer coating 215 extends over only a part of the primary cylinder 10 and namely over most of it. The upper region of the primary cylinder is free from the outer coating. The latter constitutes the contact zone A, which corresponds to the cortical zone, whilst contact zone B corresponding to the spongiosa carries the outer coating 215.

In order to break down or reduce the torque, horizontal forces transferred to the fitting cap 330 and consequently to the head 315 of oscillating rod 211 of secondary cylinder 100 lead to the oscillation of rod 211, so that a torque is formed. This torque is reduced by means of the oscillating rod in the following way. Implant attachment 240 or 240a slides on the surface 212 of primary cylinder 10 and part of the torque is consumed by the resulting sliding friction. In the case of the implant according to FIG. 7, this sliding surface 212 is constructed as a cup and advantageously has an angle $\alpha$ of 9.27°. As the implant attachment 240 or 240a slides in region 240c on primary cylinder 10, no tilts or breaks can occur, as can be the case with exactly planar surfaces and high surface pressures, if same are provided. The surfaces slide in moist and not dry manner on one another. This moisture is ensured by the use of an alumina ceramic, which has the property of making available free oxygen ions on its surface, which are automatically combined to form a free lubricant film with substances from the surrounding medium. The material ensures a self-lubrication on the sliding surface in this way and this property of alumina ceramic leads to a high self-lubricating action.

The upper modular tube 220 is made from a highly elastic material and acts as a vibration damper. As a result of this damping, more of the torque is broken down into heat. Below the upper modular tube 220 is located air gap 225, so that in its oscillating region, oscillating rod 211 of the secondary cylinder 100 inserted in primary cylinder 10 can oscillate freely. The oscillations which occur are broken down or converted into heat.

The embodiment shown in FIGS. 7 and 9 has an implant attachment 240a with a different shape to attachment 240. Implant attachment 240a is constructed as a roughly cylindrical shaped member, whose outer wall surface 240b is drawn in arcuately and whose lower external diameter approximately corresponds to the external diameter of primary cylinder 10, whilst the upper external diameter is the same or larger than that of primary cylinder 10.

Below air gap 225 is provided in the inner area of primary cylinder 10 a guide tube 30, which is bonded into said cylinder. The oscillating rod 211 of secondary cylinder 100 is anchored in true fitting manner in guide tube 30. Heat seal 250 is located on oscillating rod 211 in the upper region of guide tube 30.

As a result of the anchoring by means of the heat seal and by fitting into guide tube 30, torques reduced in the aforementioned manner are not transferred to the primary cylinder 10 via guide tube 30 throughout the bearing zone of oscillating rod 211 and specifically not in punctiform manner in the vicinity of heat seal 250 and instead they are distrubited over the entire area of guide tube 30. The remaining torques given off in distributed manner in this way over the bones are so small, that they no longer impair the firm connection of the primary cylinder to the bone produced through the hydroxyl-apatite coating 215 of the outer cylinder. This "energy-decreasing" and "bearing-protecting" mechanism makes it possible for the first time to use primary cylinders made from alumina ceramics with a wall thickness of only 0.9 mm and consequently to produce for the first time a late implant with a diameter of only 4 mm made from body-friendly alumina ceramic, because as a result of this torque-reducing mechanism there is scarcely and mechanical stressing of the primary cylinder 10.

An air layer 320 (FIG. 4) is located between oscillating head 315 of oscillating rod 211 of secondary cylinder 100 (bottom of the cone) and implant attachment 240. Thus, the oscillating rod 211 can oscillate as a result of horizontally acting forces. It is damped by the upper modular tube 220 which, with the secondary cylinder 100 inserted, extends with a portion into the interior of the longitudinal bore 13 of primary cylinder 10. As a result of this construction, modular tube 220 simultaneously provides the guidance into primary cylinder 10. The implant attachment 240 slides on the sliding surface, which is formed by the bottom of implant attachment 240 and the top of primary cylinder 10, both surfaces being ground flat and highly polished. In the case of horizontally acting chewing forces on head 315 of oscillating rod 211 or the underlying fitting cap 330, secondary cylinder 100 moves on primary cylinder 10. The horizontal displacement is 150$\mu$, which corresponds to the mobility of the natural paradontium. The mechanism which brings about the imitation of the natural paradontium is completely maintenance-free.

It is also important that as a result of its construction, the implant ensures a high gap sealing action. The implant is actually only made from two parts, namely primary cylinder 10 and secondary cylinder 100. The heat seal 250 used comprises a memory metal wire 251, which runs in annular slot 312, which is formed in oscillating rod 211. Through expansion at body temperature, heat seal 250 anchors oscillating rod 211 and consequently secondary cylinder 100 in primary cylinder 10. Guide tube 30 is provided with a groove for the engagement of the heat seal. In its upper part, this groove forms a sloping plane and in its lower part a circular portion, so that when the all-round memory metal wire 251 expands, secondary cylinder 100 is drawn into primary cylinder 10. Thus, in the vicinity of the sliding surfaces between implant attachment 240 and primary cylinder 10 a gap sealing effect is obtained, which is tight to both bacteria and to moisture.

Guide tube 30 is bonded under a clearly defined pressure in primary cylinder 10, by bridging the air gap 320 between oscillating head 315 of oscillating rod 211 and fitting cap 330 and implant attachment 240 by an inelastic disc and guide tube 30 is placed in such a way that the heat seal 250 produces the maximum defined tensile strain. The dentist need then only introduce the secondary cylinder 100 under a clearly define pressure to ensure that the heat seal engages in the groove at the intended point and consequently the necessary tension and gap freedom are ensured. Actual introduction takes place through the patient biting on the fitting cap 330 using pressure measuring strips, which can be connected to a digital pressure read-off means. The aforementioned gap sealing is in particular achieved through the use of the two heat seals 250, 350 corresponding to the embodiment of FIG. 4.

Another embodiment of the implant is shown in FIGS. 10 and 11, its basic construction corresponding to that of FIG. 7. Modular tube 220 is in this case provided in its upper end region 220a with a projecting disc or ring-like portion 220b, which partly overlaps the implant attachment 240 (240a). Portion 220b extends radially over the external diameter of oscillating head 315 into the vicinity of an engagement slot 330a in fitting 330 and simultaneously ensures the formation of an air gap 320. It is possible in this way to reliably bond modular tube 220 to implant attachment 240 (240a) and to the oscillating head 315, so that it is securely joined, whilst simultaneously forming the air gap 320 (FIG. 11).

FIG. 10 shows a heat seal embodiment differing from other implant heat seal embodiments. For this purpose the oscillating rod 211 is provided with longitudinal openings 313a, 313b, 313c, 313d extending parallel to the longitudinal axis of oscillating rod 211 into the interior of a longitudenal through-bore 311a of rod 211. Bimetallic wires, e.g. of memory metal are inserted through the longitudenal bore 311a into the interior of oscillating rod 211 in such a way that they extend outwards through longitudenal openings 313a, 313b, 313c, 313d and in the case of secondary cylinder 100 being fitted in primary cylinder 10 are in contact with guide tube 30 of the latter.

This also ensures that the oscillating rod 211 is reliably held in guide tube 30 in the bearing region, so that a large-area energy transfer to primary cylinder 10 is permitted of that energy not already converted into heat in the oscillation zone.

The enossal implant shown in FIGS. 12 to 19 also comprises primary cylinder 10 and secondary cylinder 100 and is constructed in accordance with the implant of FIGS. 4 to 11. However, this implant does not have a heat seal 250 in oscillating rod 211. The same parts carry the same references in FIGS. 12 to 19. The secondary cylinder 100 is inserted in primary cylinder 10 prior to the implantation of the complete implant.

In addition, oscillating rod 211 of secondary cylinder 100 is held in the primary cylinder 10 by means of an adhesive joint. Oscillating rod 211 with its bottom end is fixed by an adhesive joint to guide tube 30. However, it is also possible to construct primary cylinder 10 without a guide tube 30, so that then the oscillating rod 211 with its bottom end is directly held on the wall surface of longitudinal bore 13 of primary cylinder 10 by means of the adhesive joint.

There is also a possibility of arranging the oscillating rod 211 of secondary cylinder 100 in the centre of primary cylinder 10 or guide tube 30 and to fix to guide tube 30 or the wall surface of longitudinal bore 13 of primary cylinder 10 by means of the adhesive connection, the connecting zone only having to extend over a short portion.

The fitting cap 330 can be fixed to oscillating head 315 by means of a heat seal, 350 in FIG. 12. This heat seal 350 is made from a bimetallic wire 351, e.g. of memory metal, which is held in an annular slot 316 in fitting head 315 (FIG. 14). As shown in FIG. 14, the fitting head 315 tapers conically upwards.

Below air gap 225, guide tube 30 is located in the inner area of primary cylinder 10, said tube 30 being bonded into cylinder 10. The oscillating rod 211 of secondary cylinder 100 is anchored in true to size form in guide tube 30 and is also held therein by an adhesive connection, it also being possible for the latter to extend over the entire region of tube 30.

Through the anchoring of oscillating rod 211 by means of the adhesive connection and by fitting into guide tube 30, here again the torques not reduced in the aforementioned manner in the entire bearing area of oscillating rod 211 are transferred by guide tube 30 to primary cylinder 10 and are distributed over the entire area of tube 30, instead of in punctiform manner in the vicinity of the adhesive joint. The remaining torques supplied in distributed manner to the bones in this way are so small, that they no longer impair the firm connection between the primary cylinder and the bones produced by means of the hydroxyl-apatite coating 215 of the external cylinder of cylinder 10. This "energy-reducing" and "bearing-protecting" mechanism also makes it possible for the first time to use an alumina ceramic primary cylinder with a wall thickness of only 0.9 mm and consequently for the first time make it possible to produce a late implant with a diameter of only 4 mm from a body-friendly alumina ceramic material, because as a result of this torque-reducing mechanism primary cylinder 10 is scarcely mechanically stressed.

Guide tube 30 is bonded under a clearly defiined pressure in primary cylinder 10, in that the air gap 320 between oscillating head 315 of oscillating rod 211 and fitting cap 330 and implant attachment 240 is bridged by an inelastic disc.

According to FIG. 20, the implantation of an implant comprising a primary cylinder and a secondary cylinder takes place in the following way, the individual steps being designated A, B, C and D. The jawbone is 410 and for simplifying the description, a planar configuration of the jawbone surface is assumed.

The preparation of the bore for receiving implant 400 is called stage A. Firstly a depression 405 is milled in jawbone 410, which has a larger diameter than the actual bore 406 to be made, but its depth is less than the length of implant 400, as can be gathered from FIG. 20. On milling depression 405 simultaneously a centering recess is formed, which forms the centre for bore 405 to be made. After producing depression 405, bore 406 is made, whose length is somewhat less than that of implant 400, so that the connecting attachment 401 of implant 400 comes to rest in depression 405, as represented in stage B in FIG. 20.

After inserting implant 400 corresponding to stage B, the healing in of the implant takes place without loading and prior to the occurence of a bone atrophy, which is indicated by hatched portions at 408 in FIG. 20. The mucous membrane 407 closes the depression 405 above implant 400, whereof a portion extends into depression 405. Following incorporation, the connecting attachment can be provided with a cap, which fills depression 405 and consequently prevents any bone re-formation.

This is followed by bone atrophy and namely a provoked atrophy, which is given by the depth of depression 405 and the length of the implant portion extending into depression 405. Following incorporation, the connecting attachment can be provided with a cap, which fills depression 405 and consequently prevents any bone re-formation.

Even as atrophy advances, the mucous membrane 407 adapts to the advancing bone shrinkage and engages on implant 400 in the bottom area of depression 405. Following incorporation, the connecting attachment can be provided with a cap, which fills depression 405 and consequently prevents any possible bone re-formation. When bone atrophy stops, implant 400 with its connecting attachment 401 projects out of mucous membrane 407, as indicated by stage C. The healing phase can also be shortened in that the mucous membrane still covering the implant is opened above the latter when atrophy has been completed and consequently exposes the implant head, which is always advantageous if the implant is inserted deep into the jawbone. Then, according to stage D of FIG. 20, the prosthesis mount 403 is fixed, followed by the fitting of the prosthesis and the screwing down of the mount.

Stages B and C of FIG. 20 represent the first phase of implantation, namely the complete implant is implanted in the bore formed in the jawbone, which is possible because the secondary cylinder inserted in the primary cylinder is fixed to the latter. In the second phase the prosthesis mount is screwed down and then the prosthesis introduced. The preparatory depression and the bore for inserting the implant can be included in the first phase. FIG. 15 shows the different mucous membrane and jawbone limits in the old implantation method and in that according to the invention. When using the old method, according to which firstly the primary cylinder is implanted and then the secondary cylinder is inserted in the primary cylinder and connected therewith, the mucous membrane limit is indicated at a1 and the bone limit at a2. When using the process according to the invention, the mucous membrane limit and jawbone limit are at b, c being the bone limit after atrophy.

FIG. 21 shows an implant comprising primary cylinder 10 and secondary cylinder 100, whose oscillating rod 211 is fixed in the inner area of the primary cylinder by means of a screw thread 536 in a shaped body 535, which is fixed in the interior of the primary cylinder by means of an adhesive joint 537. In this embodiment, the guide tube is replaced by the shaped body 535, which is constructed in such a way that the cavity otherwise taken up by the guide tube is filled, including the gap formed between the bottom end of oscillating rod 211 and the inner base surface of primary cylinder 10. The shaped body 535 has a top bore, which is provided with an internal thread, in which engages the external thread at the end of the oscillating rod 211, so that the screw connection 536 can be made after inserting oscillating rod 211 into shaped body 535. Otherwise the implant is constructed in accordance with the embodiment of FIG. 18 and is provided with implant attachment 240 or 240a and oscillating head 315, which is surrounded by the fitting cap 330. The upper region of the oscillating rod 211 is supported on the inner wall surface of modular tube 220.

In the aforementioned examples, primary cylinder 10 and secondary cylinder 100 are made from ceramic materials. The primary cylinder is introduced through the cortical zone into the spongiosa, the primary stability being achieved by positive engagement between the implant and the implant bed on the one hand and by non-positive engagement of the attachment of the bone tissue to the alumina ceramic surface of the primary cylinder on the other.

In place of heat seals or other fastening systems for the oscillating rod 211 in primary cylinder 10, it is also possible to use detachable or undetachable clamp fasteners, as shown at 31 in FIG. 2. In the case of the embodiment shown in FIG. 22, the oscillating rod 211 of secondary cylinder 100 is held in primary cylinder 10 by a detachable clamp fastener. Therefore the guide tube 30 held in primary cylinder 10 in its base region by means of an adhesive joint has a limited length, in whose interior is arranged a shaped member 600, constructed as a solid cylinder and made from a metallic or some other suitable material, which can be fixed by an adhesive joint to guide tube 30. This shaped member 600 advantageously has a length corresponding to that of guide tube 30.

Shaped member 600 is provided on its side 601 facing modular tube 220 with a spherical or some other geometrically shaped mount 602, which is surrounded by a capsule-like element 603, which is shaped onto the bottom end of oscillating rod 211. Shaped member 600 is constructed in one piece with its mount 602. In the same way, element 603 is constructed at the bottom end of oscillating rod 211 and is secured thereto.

This capsule-like element 603 on oscillating rod 211 carries on its inner wall surface 603a facing mount 602 a bimetallic strip 604, which can e.g. be of memory metal. This bimetallic strip 604 can be incorporated into the material of the capsule-like element 603. However, it is also possible for the bimetallic strips 604 to be arranged in the form of an inner coating or insert on the inner wall surface of element 603. The complete mount 602 can also be made from memory metal.

The capsule-like element 603 is mounted on the spherical mount 601 in the supercooled state of the bimetallic strip or memory metal used, so that on warming or heating the strip, i.e. the capsule-like element 603 surrounds the spherical mount 602, so that the oscillating rod 211 of secondary cylinder 100 inserted in primary cylinder 10 is held firmly on shaped member 600, but it is possible as a result of the construction of the clamping connection to remove secondary cylinder 100 from primary cylinder 10. Mount 602 can also be made from a resilient elastic material.

According to FIGS. 23 to 26, both the oscillating rod 211 of secondary cylinder 100 in primary cylinder 10 and the fitting head 330 on oscillating rod 211 are secured by means of a clamp fastener made from a memory metal. These two clamp fasteners are shown at 630 and 630a in FIG. 23. In this enossal implant embodiment, no guide tube 30 is provided in the longitudenal bore of primary cylinder 10. In the bottom region of primary cylinder 10, shaped member 600 is inserted in its longitudenal bore and is connected to the inner wall surface of said cylinder by an adhesive joint. The upper region of said shaped member 600 carries the spherical mount 602, which is surrounded by the capsule-like, memory metal element 603, which is fixed to the lower end of oscillating rod 211. Clamp fastener 630a is constructed in the same was as fastener 630 and secures fitting head 330 on oscillating rod 211 (FIGS. 23, 24 and 26). This clamp fastener 630 is formed by the spherical mount 602a, which is constructed on the upper end of oscillating rod 211. The counter-element, namely the capsule-like memory metal element 603a is constructed in the actual fitting head 330 (FIG. 26). FIG. 26 shows the capsule-like element 603a before deformation for the engagement position.

According to another embodiment, instead of bimetallic strip 604, the capsule-like element 603 can be provided on its inner wall surface with a coating, insert or the like made from a permanent elastic material, such as e.g. a polyurethane elastomer or some other suitable elastic material. The use of a bimetallic strip ensures that if it expands the secondary cylinder 100 is drawn against the primary cylinder 10, so that in this way the friction of the spherical sliding surfaces of secondary cylinder 100 and implant attachment 240 can be metered. Otherwise the construction of the implant according to FIG. 22 is like that of the implant of FIG. 7. Guide tube 30 need not have the short length shown in FIG. 22. It is also possible to provide guide tube 30 with the length shown in FIG. 7, the shaped member 600 then being fixed by an adhesive joint in the bottom region of guide tube 30 and can then have a shorter length than member 600.

In the embodiment of FIGS. 27 to 30, the oscillating rod 211 is held in primary cylinder 10 by means of an undetachable clamp fastener 640. To this end guide tube 30, whose lower region is fixed in primary cylinder 10 by means of an adhesive joint, is constructed in its bottom region as a solid cylinder. The resulting shaped member is designated 610 and is made from a metallic or some other suitable material. This shaped member 610 forms with the guide tube 30 a unit, the length of shaped member 610 representing roughly half the total length of shaped member 610/guide tube 30.

The shaped member 610 formed in the upper region as guide tube 30 is provided with a top bore 611. In the vicinity of the inner wall surface 611a of the bore is formed at least one annular slot 612, which is radially directed and e.g. has a triangular cross-section, whilst the oscillating rod 211 has on the outer periphery of its bottom end constructed as a pin 211a, a plurality of bead-like rings 613 engaging in the anular slot 612 when oscillating rod 211 is inserted in bore 611 of shaped member 610 corresponding to the number of annular slots 612 in bore 611 of shaped member 610. The number of annular slots 612 in bore 611 of shaped member 610 can be selected at random. One annular slot 612 is in itself sufficient for a firm seat of oscillating rod 211 in primary cylinder 10 (FIGS. 27, 28 and 29).

In the same way as oscillating rod 211 of secondary cylinder 100 is held in primary cylinder 10 using shaped member 610, it is also possible to fix fitting head 330 onto the free upper end of oscillating rod 211, whereof a portion of its upper end projects out of the implant attachment 240. The clamp fastener for the fitting cap 330 is designated 640a and is constructed in accordance with the clamp fastener 640 (FIG. 27). The fitting cap 330 is provided with a bore 611b, which has an annular slot 612a on the inner wall side (FIG. 30). The upper free end of oscillating rod 211 is constructed in such a way that it can be inserted in bore 611b. Oscillating rod 211 carries at its upper outer periphery a ring-like bead 613a, which is profiled in such a way that after mounting fitting cap 330 on oscillating rod 211 it engages in the annular slot 612a in fitting head 330 (FIG. 29). By inserting the individual parts, whilst applying a slight pressure, the clamp fasteners 640, 640a are formed (FIG. 27).

FIG. 31 shows two different constructions of a clamp fastener A, B. In embodiment A, concentric annular slots 612 are provided, whilst oscillating rod 211 carries concentric, bead-like rings 613 on its outer circumference, which are constructed and arranged in such a way that after inserting oscillating rod 211 in primary cylinder 10, said rings 613 engage in the annular slots 612.

In the case of the embodiment indicated at B, annular slots 612 or the annular slots of bore 611 of shaped member 610 have an approximately triangular cross-section for forming upper undercuts 614, whilst the oscillating rod 211 is provided on its bottom outer circumference with a plurality of ring-like engagement profiles 615 corresponding to the number of annular slots 612, so that after inserting the bottom end of rod 211 in bore 611 of shaped member 610, said engagement profiles 615 engage in slots 612, so that as a result of the aforementioned design, it is not possible to detach or release the clamp fastener.

The gap sealing between the two spherical sliding surfaces 212, 240c of primary cylinder 10 and implant attachment 240 or 240a is achieved through the true to size, positive bearing of the spherical sliding surfaces on one another between primary cylinder 10 and the implant attachment or the mucous membrane sleeve, which represents the ceramic upper part, and the chemisorption which is brought about by the ceramic material used, namely in that the ceramic material used gives off oxygen ions at its surface, which are combined with the surrounding medium to form a sliding coating, atmospheric humidity normally being sufficient to bring about chemisorption. Thus, a sliding or lubricating film is formed in this way through utilizing the material characteristics.

It is also possible to achieve gap sealing with a coating 620 or an insert of polytetrafluroethylene, known under the trade name Teflon, or some other suitable and in particular oxygen ion-permeable material, as shown in FIG. 32. The coating materials can in particular be those which in no way impair chemisorption. The coating can be replaced by shaped bodies in the form of inserts made from suitable materials. The coating made from the suitable materials can be applied to one of the two spherical sliding surfaces 212 or 240c.

As shown in FIG. 32, the otherwise provided air gap 225 between guide tube 30 and the upper modular tube 220 can be filled by a further modular tube 30a made from permanent elastic material placed above the guide tube 30, whereby said material can be plastic or some other suitable material. This additional modular tube 30a ensures an adequate sealing of the gaps.

The upper all-round edge of modular tube 220 is bent outwards in sleevelike manner. This bent or angular portion 220c is used for compensating the rod compression when vertical forces occur (FIGS. 27 and 29).

We claim:

1. Enossal implant for the securing of a fixed or removable dental prosthesis, comprising two interconnectable parts, whereof one part is constructed as a primary cylinder (10) with a central longitudinal bore (13), which can be introduced into the jawbone and is anchored therein and the other part is constructed as a secondary cylinder (100) having a post (111), which can be introduced into the longitudinal bore of the primary cylinder and is detachably held therein, said post being constructed as its free upper end for the connection of the dental prosthesis, characterized in that the implant post (150) of the secondary cylinder (100) is surrounded by a force line system (101, 102, 103) diverting the horizontal, vertical, torsional or any combination of the three forces and oscillations occuring in the vicinity of the dental prosthesis or mouth into the lower region of the secondary cylinder (100) and from there into the primary cylinder (10), said system comprising several superimposed modular members (101, 102, 103, 104) with different elastic characteristics, in such a way that a bottom, inelastic region (103, 104) is followed by a region (102) with a limited elasticity and onto the latter is connected a region (101) with a high elasticity.

2. Enossal implant according to claim 1, characterized in that the implant post (150) is made from a ceramic material, the implant post (150) being surrounded.

3. Enossal implant according to claim 1 or 2, further comprising an implant attachment (106), characterized in that said force line system (101, 102, 103, 104) surrounding the implant post (150) comprises at least one lower modular member (104, 103) made from inelastic material, a central modular member (102) following onto the same and made from a material with limited elasticity and an upper modular member (101) following onto the same made from a highly elastic material, the upper modular member (101) extending into said implant attachment (106).

4. Enossal implant according to claim 3, characterized in that said modular members (101 to 104) have approximately equal lengths.

5. Enossal implant according to claim 3, characterized in that a guide tube (30) as an elatically deformable intermediate layer is placed in the longitudinal bore (13) of primary cylinder (10) and receives the implant post (150) with said modular members (101 to 104) surrounding the same.

6. Enossal implant according to claim 1, characterized in that the primary cylinder (10) has a bearing surface (15) for implant attachment (106) and an upper all-round edge (14), the bearing surface (15) and edge (14) being highly polished over a width of 1 to 5 mm.

7. Enossal implant according to claim 1, characterized in that the primary cylinder (10) is made from titanium.

8. Enossal implant according to claim 1, characterized in that said primary cylinder (10) is externally coated with hydroxyapatite (11).

* * * * *